United States Patent [19]
Brunck et al.

[11] Patent Number: 5,883,077
[45] Date of Patent: Mar. 16, 1999

[54] INHIBITORS OF FACTOR XA

[75] Inventors: Terence Kevin Brunck, San Diego; Thomas Roy Webb, Encinitas; William Charles Ripka, San Diego, all of Calif.

[73] Assignee: Corvas International, Inc., San Diego, Calif.

[21] Appl. No.: 168,964

[22] Filed: Dec. 15, 1993

Related U.S. Application Data

[63] Continuation-in-part of Ser. No. 991,204, Dec. 15, 1992, abandoned.

[51] Int. Cl.$^6$ ..................................................... C07K 5/06
[52] U.S. Cl. ............................... 514/19; 530/331; 518/18
[58] Field of Search ................................. 530/331, 330; 514/18

[56] References Cited

U.S. PATENT DOCUMENTS

| | | | |
|---|---|---|---|
| 4,847,201 | 7/1989 | Kaswasaki | 435/70 |
| 4,882,145 | 11/1989 | Thornton | 424/88 |
| 4,883,863 | 11/1989 | Abe et al. | 530/331 |
| 5,141,862 | 8/1992 | Patel | 435/226 |
| 5,153,176 | 10/1992 | Abe et al. | 514/18 |
| 5,283,293 | 2/1994 | Webb | 525/332.2 |
| 5,367,072 | 11/1994 | Webb | 540/483 |

FOREIGN PATENT DOCUMENTS

| | | |
|---|---|---|
| 9308211 | 4/1993 | WIPO . |
| WO 93/08211 | 4/1993 | WIPO ............................................. 5/6 |
| WO 93/12076 | 6/1993 | WIPO . |

OTHER PUBLICATIONS

Ripka et al., Strategies in the Design of Inhibitors of Serine Proteases of the Coagulation Cascade–Factor Xa, *Eur. J. Med. Chem.*, Supplement to vol. 20, pp. 87s–110s (1995).

R.M. McConnell et al., *Journal of Medicinal Chemistry 33:1*, pp. 86–93 (Jan. 1990).

A.M. Murphy et al., *Journal of American Chemical Society 114:8*, pp. 3156–3157 (Apr. 1992).

R.M. McConnell et al., *Journal of Medicinal Chemistry 36:8*, pp. 1084–1089 (Apr. 1993).

*Primary Examiner*—Cecilia J. Tsang
*Assistant Examiner*—David Lukton
*Attorney, Agent, or Firm*—Lyon & Lyon LLP

[57] ABSTRACT

Novel compounds, their salts and compositions related thereto having activity against mammalian factor Xa are disclosed. The novel compounds include peptide aldehyde analogues having substantial potency and specificity as inhibitors of mammalian factor Xa are further disclosed. The compounds are thought useful as inhibitors of factor xa in vitro or as a therapeutic agent for the prevention and treatment of conditions characterized by abnormal thrombosis in mammals. Intermediates useful for the preparation of the novel compounds are also disclosed.

13 Claims, 3 Drawing Sheets

5,883,077

INHIBITORS OF FACTOR XA

RELATED APPLICATIONS

This application is a continuation-in-part of U.S. Ser. No. 07/991,204, filed Dec. 15, 1992, now abandoned entitled "Novel Inhibitors of Factor Xa", the disclosure of which is hereby incorporated by reference including the drawings attached thereto.

FIELD OF THE INVENTION

The present invention relates in one aspect to compounds, their pharmaceutically acceptable salts and pharmaceutically acceptable compositions thereof which are potent and specific inhibitors of blood coagulation in mammals. The inhibition of clot formation flows from the direct inhibition of the blood coagulation enzyme, factor xa, by the inhibitors disclosed. In another aspect, the invention relates to a methods of using these inhibitors in their various embodiments as therapeutic agents for disease states characterized by disorders of the blood coagulation process. In yet another aspect, the invention relates to intermediate compounds useful in the preparation of the inhibitors.

BACKGROUND AND INTRODUCTION TO THE INVENTION

Normal hemostasis is the result of a complex balance between the processes of clot formation (blood coagulation) and clot dissolution (fibrinolysis). The complex interactions between blood cells, specific plasma proteins and the vascular surface maintain the fluidity of blood unless injury and blood loss occur. Many significant disease states are related to abnormal hemostasis. Abnormal thrombus formation occurring in the coronary arterial vasculature due to the rupture of an established atherosclerotic plaque is the major cause of acute myocardial infarction and unstable angina. Treatment of occlusive coronary thrombus by either thrombolytic therapy or percutaneous transluminal angioplasty is often accompanied by an acute thrombotic reclosure of the affected vessel which requires immediate resolution. A high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs during septic shock, certain viral infections and cancer and is characterized by the rapid consumption of coagulation factors and systemic coagulation which results in the formation of life-threatening thrombi occurring throughout the vasculature leading to wide-spread organ failure.

Blood coagulation is the culmination of a series of amplified reactions in which several specific zymogens of serine proteases in plasma are activated by limited proteolysis. This results in the formation of an insoluble fibrin matrix which is required for the stabilization of the primary hemostatic plug. The interaction and propagation of the activation reactions occurs through the extrinsic and intrinsic pathways of coagulation as reviewed by Mackie, I. J. and Bull, H. A., "Normal Hemostasis and its Regulation" Blood Reviews, 3: 237–250 (1989). Both pathways are highly inter-dependent and converge in the formation of the serine protease factor xa from its zymogen, factor X. Factor Xa catalyzes the penultimate step in the blood coagulation cascade which is the formation of the serine protease thrombin. Thrombin goes on to cleave soluble fibrinogen in the plasma to form insoluble fibrin.

The biochemical and physiological characterization of factor X has been reviewed by Steinberg, M. and Nemerson, Y., "Activation of Factor X", Hemostasis and Thrombosis, First Edit., pp 91–111 (Colman, R. et. al. eds. 1982) and Mann, K. G. et. al., "Surface-Dependent Reactions of the Vitamin K-Dependent Enzyme Complexes", Blood, 76: 1–16 (1990). Human factor X circulates in plasma at a concentration of 170 nM. The enzyme is a two-chain glycoprotein containing 442 amino acid residues having an overall molecular size (Mr) of 59,000 as determined by sedimentation equilibrium centrifugation and approximately 67,000 by sodium dodecyl sulfate electrophoresis. DiScipio et. al., "A comparison of human prothrombin, Factor IX (Christmas Factor), Factor X (Stuart Factor) and Protein S", Biochemistry, 16: 698–706 (1977) and Leyfus et. al., "Characterization of a cDNA coding for human Factor X", Proc. Natl. Acad. Sci. USA, 82: 3699 (1984). Human factor X contains a light-chain subunit containing 139 amino acid residues (Mr=16,200) and a heavy chain subunit containing 303 amino acid residues (Mr=42,000) linked together by a single disulfide bond. The light chain of human factor X contains 11 glutamic acid residues which have been post-translationally modified to γ-carboxy-glutamic acid and one asparagine acid moiety modified to β-hydroxy aspartic acid. The heavy chain of factor X contains all of the glycosylated residues (15% overall) as well as the catalytic domain of the molecule.

Proteolytic activation of zymogen factor X to its catalytically active form, factor Xa, can occur by either the intrinsic or extrinsic coagulation pathways. The intrinsic pathway is referred to as intrinsic because everything needed for clotting is in the blood. Saito, H., "Normal Hemostatic Mechanisms", Disorders of Hemostasis, pp. 27–29, Grune & Stratton, Inc. (O. D. Ratnoff, M.D. and C. D. Forbes, M.D. edit. 1984). This pathway is comprised of the zymogen serine proteases, factors IX and XI, and the non-enzymatic co-factor, factor VIII. The initiation of the intrinsic pathway results in the activation of factor XI to XIa. Factor XIa catalyzes the activation of factor IX to factor IXa which in combination with the activated form of factor VIII on an appropriate phospholipid surface, results in the formation of the tenase complex. This complex also catalyzes the formation of the serine protease, factor Xa, from its zymogen, factor X, which subsequently results in clot formation.

The extrinsic pathway is referred to as extrinsic because the tissue factor which binds to and begins activation of factor VII comes from outside the blood. Saito, Id, The major components of this pathway are the zymogen serine protease, factor VII, and the membrane bound protein, tissue factor. The latter serves as the requisite non-enzymatic co-factor for this enzyme. The initiation of this pathway is thought to be an autocatalytic event resulting from the activation of zymogen factor VII by trace levels of activated factor VII (factor VIIa), both of which are bound to newly exposed tissue factor on membrane surfaces at sites of vascular damage. The factor VIIa/tissue factor complex directly catalyzes the formation of the serine protease, factor Xa, from its zymogen, factor X. Exposure of blood to injured tissue initiates blood clotting by the extrinsic pathway.

Proteolytic activation of zymogen factor X to its catalytically active form, factor Xa, results in the liberation of a 52 amino acid activation peptide from the amino-terminus of the heavy chain subunit. The intrinsic activation reaction is catalyzed by factor Ixa in a macromolecular complex with the non-enzymatic co-factor, factor VIII. Factor Xa formation via the extrinsic pathway is catalyzed by the catalytic complex of factor VIIa and tissue factor. Both of these reactions must occur on an appropriate phospholipid surface in the presence of calcium ions. The active product formed following either intrinsic or extrinsic activation of factor X is α-factor Xa. A second proteolytic cleavage which is thought to be autocatalytic, results in the formation of β-factor Xa following the release of a 14 amino acid peptide from the carboxy-terminus of the heavy chain. Both forms of the activated molecule have the same catalytic activity as measured by their ability to promote coagulation in plasma or hydrolyze a peptidyl chromogenic substrate.

The formation of thrombin is catalyzed by factor Xa following the assembly of the catalytic prothrombinase complex as reviewed by Mann, K. G. et. al., "Surface-Dependent Reactions of the Vitamin K-Dependent Enzyme Complexes", Blood, 76: 1–16 (1990). This complex is composed of factor xa, the non-enzymatic co-factor Va and the substrate prothrombin all assembled on an appropriate phospholipid surface. The requirement of a macromolecular complex for efficient catalysis results in the protection of factor Xa from natural anticoagulant mechanisms such as heparin-antithrombin III mediated inhibition. Teite, J. M. and Rosenberg, R. D., "Protection of Factor Xa from neutralization by the heparin-antithrombin complex", J. Clin. Invest., 71: 1383–1391(1983). In addition sequestration of factor Xa in the prothrombinase complex also renders it resistant to inhibition by exogenous heparin therapy which also requires antithrombin III to elicit its anticoagulant effect.

Several examples of naturally occurring polypeptide inhibitors of factor Xa have been reported to have excellent specificity and potency. U.S. Pat. No. 4,588,587 to Gasic describes the anticoagulant activity of Haementeria offcinalis leech saliva. A principal component of the leech saliva, Antistasin was said to inhibit factor xa. See, Tuszynski, G. P. et. al., "Isolation and characterization of antistasin, an inhibitor of metastasis and coagulation", J. Biol. Chem., 262: 9718–9723 (1987); Nutt, E. et. al.,"The amino acid sequence of antistasin, a potent inhibitor of Factor xa reveals a repeated internal structure", J. Biol. Chem., 63: 10162–10167 (1988); Dunwiddie, C. et. al., "Antistasin, a leech-derived inhibitor of factor Xa, kinetic analysis of enzyme inhibition and identification of the reactive site", J. Biol. Chem., 264:16694–16699 (1989); and Han, J. H. et. al., "Cloning and expression of cDNA encoding antistasin, a leech-derived protein having anti-coagulant and anti-metastatic properties", Gene, 75: 47–57 (1989).

A polypeptide reported to be a selective and potent inhibitor of factor Xa was originally isolated from whole body extracts of the soft tick Ornithidoros moubata. See Waxman, L. et. al., "Tick anticoagulant peptide (TAP) is a novel inhibitor of blood coagulation factor Xa", Science, 248: 593–596(1990); Neeper M. P. et al.,"Characterization of recombinant tick anticoagulant peptide, a highly selective inhibitor of blood coagulation, factor Xa", J. Biol. Chem., 265: 17746–17752 (1990); and Jordan, S. P. et. al., "Tick anticoagulant peptide: kinetic analysis of the recombinant inhibitor with blood coagulation factor Xa", Biochemistry, 29: 11095–11100 (1990); and Vlasuk et al., U.S. Pat. No. 5,239,058 (Aug. 24, 1993).

Plasma has been reported to contain a common inhibitor of both factor Xa and factor VIIa-tissue factor complex called lipoprotein-associated coagulation inhibitor (LACI). LACI is reported to consist of 276 amino acids and has been reported to inhibit the proteolytic activity of factor Xa directly, and in a factor Xa-dependent manner, factor VIIa-tissue factor complex. Girard, T. J. et al., Nature, 338: 518–520 (1989).

Other polypeptide inhibitors of factor Xa have also been reported. See, e.g., Jacobs, J. W. et. al., "Isolation and characterization of a coagulation factor Xa inhibitor from Black fly salivary glands", Thromb. Haemostas., 64: 235–238 (1990); Condra, C. et. al., "Isolation and structural characterization of a potent inhibitor of coagulation factor Xa from the leech Haementeria ghilianii", Thromb. Haemost., 61: 437–441 (1989); Brankamp, R. G. et. al., "Ghilantens: anticoagulants, antimetastatic proteins from the South American leech Haementeria ghilianii", J. Lab. Clin. Med., 115: 89–97 (1990); Blankenship, D. T. et. al., "Amino acid sequence of ghilanten: anti-coagulant-antimetastatic principle of the South American leech, Haementeria ghilianii"", Biochem. Biophys. Res. Commun., 166: 1384–1389 (1990); and Rigbi, M. et. al.,"Bovine factor Xa inhibiting factor and pharmaceutical compositions containing the same", European Patent Application, publication no. 352,903 (1990).

In addition to the above polypeptide inhibitors of factor Xa, small molecule inhibitors of this enzyme have been reported. See, Kam, et. al., "Mechanism based isocoumarin inhibitors for trypsin and blood coagulation serine proteases: new anticoagulants", Biochemistry, 27: 2547–2557 (1988); Tidwell, R. R. et. al., "Strategies for anticoagulation with synthetic protease inhibitors. Xa inhibitors versus thrombin inhibitors", Thromb. Res., 19: 339–349 (1980); Hitomi, Y. et. al., "Inhibitory effect of a new synthetic protease inhibitor (FUT-175) on the coagulation system", Haemostasis, 15: 164–168 (1985); Turner, A. D. et. al., "p-Amidino esters as irreversible inhibitors of factors IXa and Xa and thrombin", Biochemistry, 25: 4929–4935 (1986); and Sturzebecher, J. et. al., "Synthetic inhibitors of bovine factor Xa and thrombin. Comparison of their anticoagulant efficiency", Thromb. Res., 54: 245–252 (1989).

Unlike the reported polypeptide inhibitors of factor xa, the known small molecule inhibitors have been reported to be relatively non-selective with respect to the inhibition of other serine proteases. For example, 6-amidino-2-naphthyl-p-guanidinobenzoate dimethanesulfonate (FUT-175) inhibits human factor Xa and human thrombin similarly, yielding inhibitor constants of 4.1 $\mu$M and 1.3 $\mu$M, respectively. Hitomi et al., supra, at p. 166. p-Amidinophenyl α-methylcinnamate irreversibly inactivates human factor xa, human factor XIa and human thrombin similarly yielding second-order rate constants of inactivation of $9.9 \times 10^4$, $16 \times 10^4$, and $16 \times 10^4$ $M^{-1}$ $min^{-1}$, respectively. Turner et al., supra, at p. 4932.

SUMMARY OF THE INVENTION

In one aspect, the present invention is directed to compounds which selectively inhibit the catalytic activity of factor Xa but do not appreciably inhibit the activity of factor XIa, thrombin or tissue plasminogen activator (tPA). These compounds are characterized by having a Percent Selectivity for each of factor XIa, thrombin and tPA less than or equal to 10. Percent Selectivity is defined as 100 times the $IC_{50}$ for factor Xa divided by the $IC_{50}$ of either factor XIa, thrombin or tPA. $IC_{50}$ is that concentration of test compound giving 50% inhibition of the substrate turnover. These compounds are peptide analogs of relatively low molecular weight, namely, peptide aldehydes which have molecular weights less than about 1000. These compounds are thought to be useful either as in vitro diagnostic reagents for selectively inhibiting factor xa while only weakly inhibiting, if at all, factor XIa, thrombin or tissue plasminogen activator (tPA), or as pharmacological agents for the treatment of certain thrombotic disorders.

The novel compounds of the present invention include those represented by the formulas:

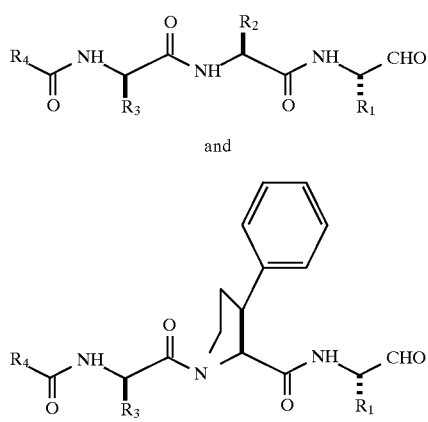

(I)

and (I')

wherein

- $R_1$ is selected from the group consisting of —$(CH_2)_3$—NH—C(=NH)—$NH_2$ and mono-and di-alkyl-substituted derivatives thereof, wherein each alkyl group is independently selected and has about 1 to about 7 carbon atoms;
- $R_2$ is selected from the group consisting of aralkyl of about 6 to about 15 carbon atoms optionally substituted with 1 to 2 independently selected alkyl groups of about 1 to about 4 carbon atoms;
- $R_3$ is selected from the group consisting of aryl of about 6 to about 14 carbon atoms optionally substituted with 1 to 2 independently selected alkyl groups of about 1 to about 4 carbon atoms, aralkyl of about 7 to about 15 carbon atoms optionally substituted with 1 to 2 independently selected alkyl groups of about 1 to about 4 carbon atoms, and alkyl of about 1 to about 7 carbon atoms; and
- $R_4$ is selected from the group consisting of alkyl of about 1 to about 12 carbon atoms, alkenyl of about 3 to about 6 carbon atoms, aryl of about 6 to about 14 carbon atoms, aralkyl of about 6 to about 15 carbon atoms, alkoxy of about 1 to about 12 carbon atoms, alkenyloxy of about 3 to about 8 carbon atoms, aryloxy of about 6 to about 14 carbon atoms, aralkyloxy of about 6 to about 15 carbon atoms, and carboxyalkyl of about 2 to about 7 carbon atoms.

The present invention also encompasses the pharmaceutically acceptable salts of the compounds of formulas (I) and (I'). These salts include acid addition salts, for example, salts of hydrochloric acid, hydrobromic acid, acetic acid, benzene sulfonic acid and other suitable acid addition salts, including buffering salts.

Peptidyl arginine aldehydes have been reported to exist in equilibrium structures in aqueous solutions. Bajusz, S., et al., J. Med Chem., 33: 1729 (1990). These structures, as shown below, include the arginine aldehyde, A, aldehyde hydrate, B, and two amino cyclol forms, C and D. The R group would represent the remainder of a given compound embodied in the present invention. The peptide aldehydes of the present invention include within their definition all its equilibrium forms.

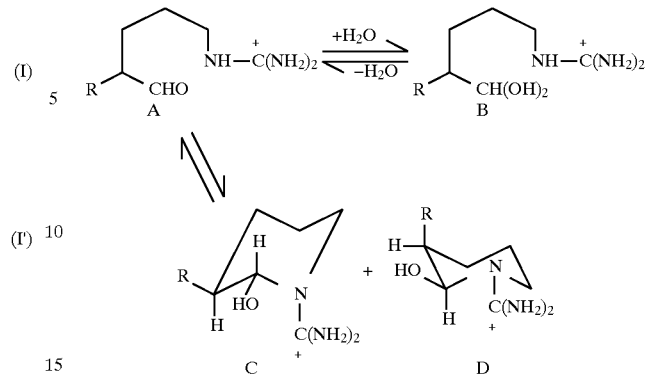

In another aspect, the present invention is directed to compounds which are intermediates for the novel compounds claimed herein. The intermediates include those represented by the formulas:

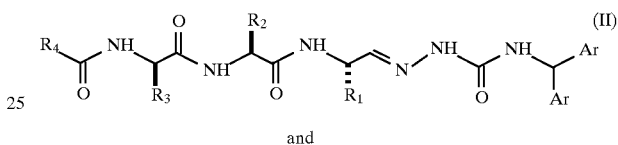

(II)

and

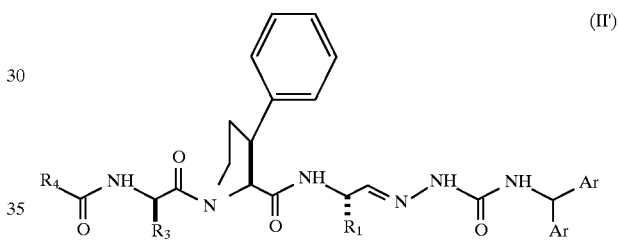

(II')

wherein Ar has the formula:

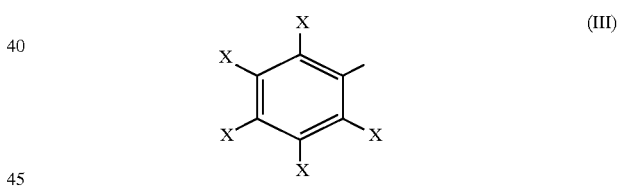

(III)

where each x is independently selected from the group consisting of hydrogen, methyl, methoxy, halogen, ethyl and ethoxy; $R_1$ is selected from a group consisting of —$(CH_2)_3$—NH—C(=$NNO_2$)—$NH_2$, and mono- or di-alkyl-substituted derivatives thereof, wherein each alkyl group is independently selected and has about 1 to about 7 carbon atoms; and $R_2$, $R_3$ and $R_4$ are as defined as for formulas (I) and (I') hereinabove.

The present invention also provides compositions and methods for preventing or treating a condition characterized by abnormal thrombus formation in mammals.

Definitions

In accordance with the present invention and as used herein, the following terms are defined with the following meanings, unless explicitly stated otherwise.

The term "alkyl" refers to saturated aliphatic groups including straight-chain, branched-chain and cyclic groups.

The term "alkenyl" refers to unsaturated hydrocarbyl groups which contain at least one carbon-carbon double bond and includes straight-chain, branched-chain and cyclic groups.

The term "aryl" refers to aromatic groups which have at least one ring having a conjugated pi electron system and includes carbocyclic aryl, heterocyclic aryl and biaryl groups, all of which may be optionally substituted.

The term "aralkyl" refers to an alkyl group substituted with an aryl group. Suitable aralkyl groups include benzyl, picolyl, and the like, and may be optionally substituted.

The term "methylene" refers to —$CH_2$—.

The term "alkylene" refers to a divalent straight chain or branched chain saturated aliphatic radical.

The term "alkoxy" refers to the group —OR, wherein R is alkyl.

The term "alkenyloxy" refers to the group —OR, wherein R is alkenyl.

The term "aryloxy" refers to the group —OR, wherein R is aryl.

The term "aralkyloxy" refers to the group —OR, wherein R is aralkyl.

The term "carboxyalkyl" refers to the group -alk-COOH, wherein alk is an alkylene group.

The term "halogen" refers to fluorine, chlorine, bromine or iodine atoms.

The term "pharmaceutically acceptable salt" includes salts of the compounds of the present invention derived from the combination of a such compounds and an organic or inorganic acid. In practice, the use of the salt form amounts to use of the base form. The compounds of the present invention are useful in both free base and salt form, with both forms being considered as being within the scope of the present invention.

In addition, the following abbreviations stand for the following:

"Ac" refers to acetyl.
"α-NpAla" refers to 3-(1-naphthyl)alanine also known as 3-(α-naphthyl)alanine.
"β-NpAla" refers to 3-(2-naphthyl)alanine also known as 3-(β-naphthyl)alanine.
"Bn" refers to benzyl.
"Boc" refers to t-butoxycarbonyl.
"BOP" refers to benzotriazol-1-yloxy-tris-(dimethylamino)-phosphonium-hexafluorophosphate.
"BPGly" refers to α-biphenylglycine.
"Brine" means an aqueous saturated solution of sodium chloride.
"CDI" refers to carbonyldiimidazole.
"DCM" refers to dichloromethane.
"DIEA" refers to diisopropylethylamine.
"DMF" refers to N,N-dimethylformamide.
"IPA" refers to isopropanol.
"MeOH" refers to methanol.
"4MeV" refers to 4-methylvaleroyl.
"NaOAc" refers to sodium acetate.
"NMM" refers to 4-methylmorpholine.
"Ph" refers to phenyl group.
"PhGly" refers to 2-phenylglycine.
"Ppa" refers to a protected peptide analog.
"Succ" refers to succinyl.
"TBSA" refers to 0.1M Tris, 0.14M sodium chloride, pH 7.4 containing 0.1% bovine serum albumin.
"TEA" refers to triethylamine.
"TFA" refers to trifluoroacetic acid.
"THF" refers to tetrahydrofuran.
"3-trans-PhPro" refers to 3-trans-phenyl-L-proline.

DETAILED DESCRIPTION OF THE INVENTION

Figure 1:
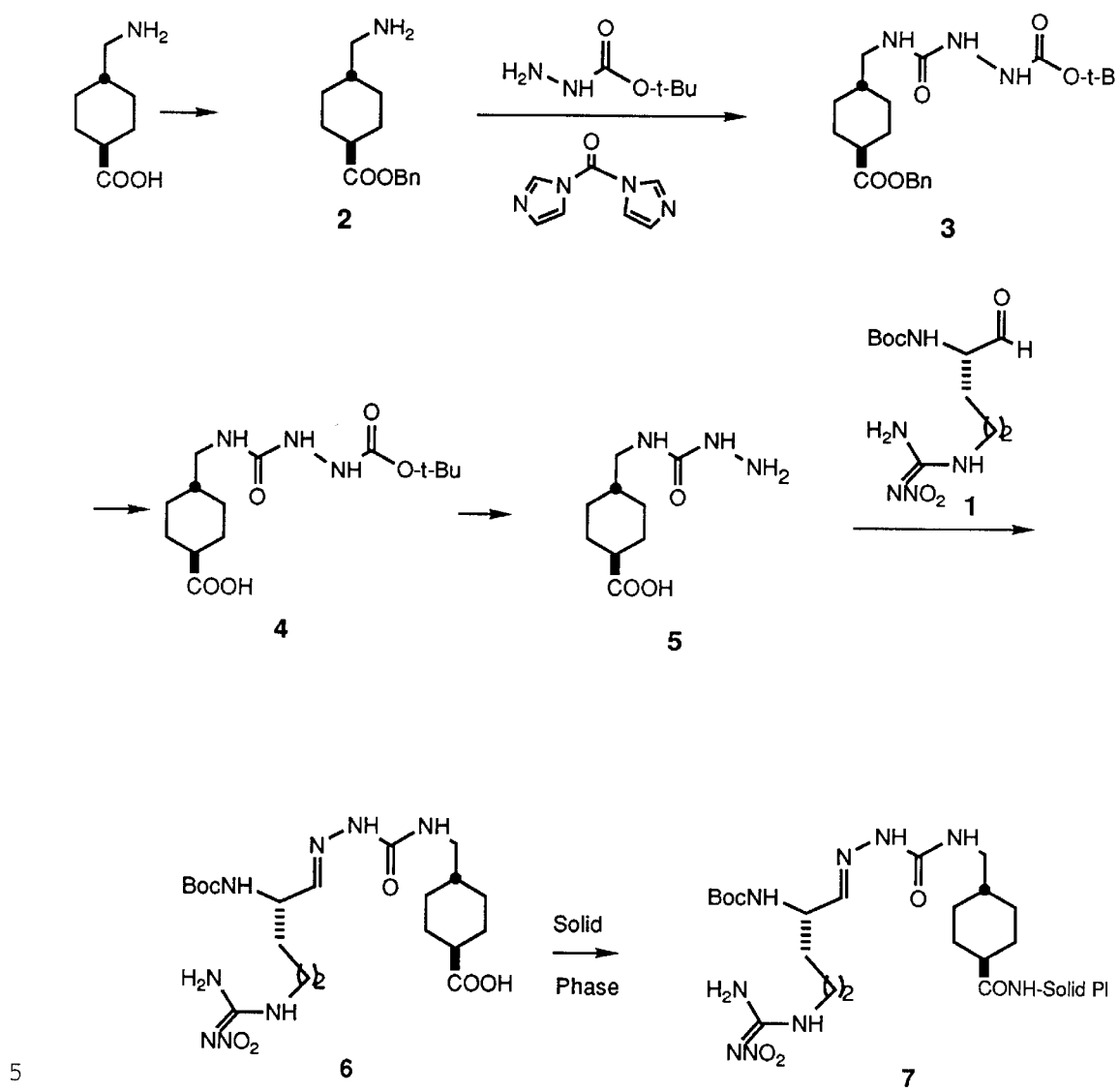
FIG. 1 depicts a reaction scheme describing a process for preparing a solid-phase reagent,1, which may be subsequently used to make one or more of the compounds of the present invention. In this figure, Bn represents to benzyl; t-Bu represents to t-butyl; and Boc represents to t-butoxycarbonyl.

The compounds of the present invention have been found to have the surprising property that they are potent inhibitors of factor Xa but only weak inhibitors of factor XIa, thrombin and tissue plasiminogen activator (tPA). Significantly, previously reported small-molecule factor Xa inhibitors which have been described as effective antithrombotic agents are nonspecific in their inhibitory activity in that they cannot distinguish between the factor Xa and other coagulation enzymes. Also, peptide aldehyde derivatives have been described as ineffective in inhibiting factor xa and this inability has been described as a limitation of the use of peptide aldehyde inhibitors in blood coagulation. Bajusz, S. et al., "Design and Synthesis of Peptide Inhibitors of Blood Coagulation", Folia Haematol., Leipzig, 109: 16 at 19 (1982).

Preferred Compounds

One aspect of the present invention is directed to N-acyl derivatives of certain peptide aldehydes. These compounds are characterized by their ability to strongly inhibit factor xa but only weakly inhibit factor XIa, thrombin and tPA. Formulas (I) and (I') below depict the compounds comprising this aspect of the present invention:

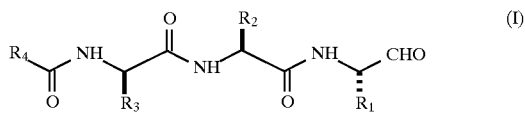

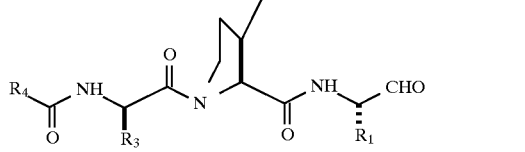

wherein
$R_1$ is selected from the group consisting of —$(CH_2)_3$—NH—C(=NH)—$NH_2$ and mono- or di-alkylsubstituted derivatives thereof, wherein each alkyl group is independently selected and has about 1 to about 7 carbon atoms;

$R_2$ is selected from the group consisting of aralkyl of about 6 to about 15 carbon atoms optionally substituted with 1 to 2 independently selected alkyl groups of about 1 to about 4 carbon;

$R_3$ is selected from the group consisting of aryl of about 6 to about 14 carbon atoms optionally substituted with 1 to 2 independently selected alkyl groups of about 1 to about 4 carbon atoms, aralkyl of about 7 to about 15 carbon atoms optionally substituted with 1 to 2 independently selected alkyl groups of about 1 to about 4 carbon atoms, and alkyl of about 1 to about 7 carbon atoms; and $R_4$ is selected from the group consisting of alkyl of about 1 to about 12 carbon atoms, alkenyl of about 3 to about 6 carbon atoms, aryl of about 6 to about 14 carbon atoms, aralkyl of about 6 to about 15 carbon atoms, alkoxy of about 1 to about 12 carbon atoms, alkenyloxy of about 3 to about 8 carbon atoms, aryloxy of about 6 to about 14 carbon atoms, aralkyloxy of about 6 to about 15 carbon atoms and carboxyalkyl of about 2 to about 7 carbon atoms.

The present invention also encompasses the pharmaceutically acceptable salts of these compounds. These salts include acid addition salts, for example, salts of hydrochloric acid, hydrobromic acid, acetic acid, benzene sulfonic acid and other suitable acid addition salts, including buffering salts.

For convenience in discussing preferred substituents, these compounds can be divided into parts as shown in the following formulas (Ia) and (Ia'):

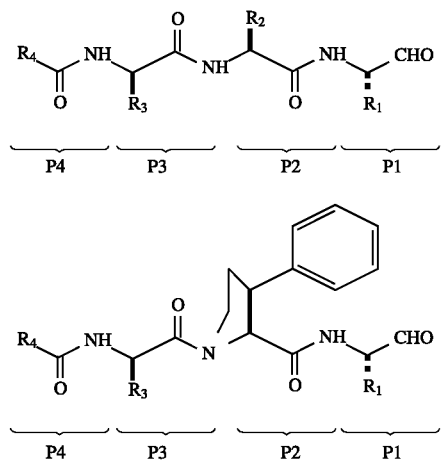

Preferred compounds include those where the $P_1$ amino acid analogue is an L-isomer. Especially preferred are the compounds wherein $R_1$ is —$(CH_2)_3$—NH—C(=NH)—$NH_2$.

These preferred compounds of formula (I) and (Ia) also contain a $P_2$ amino acid analogue which is a L-isomer, containing an $R_2$ group which is preferably an aralkyl such as phenylmethyl, diphenylmethyl, biphenylmethyl, naphthylmethyl, or mono- or di-substituted alkyl derivatives thereof, wherein each alkyl group has about 1 to about 4 carbon atoms. Especially preferred are compounds wherein is $R_2$ is phenylmethyl, 1-naphthylmethyl or 2-naphthylmethyl.

The preferred compounds of formula (I) and (Ia) or (I') and (Ia') also contain a $P_3$ amino acid analogue which is a D-isomer, containing an $R_3$ group which may be an aryl or aralkyl group suitable $R_3$ groups include groups, such as phenyl, phenylmethyl, diphenylmethyl, biphenyl, biphenylmethyl, napthyl, naphthylmethyl and or mono- or di-substituted alkyl derivatives thereof, wherein each alkyl group has about 1 to about 4 carbon atoms or alkyl groups such as cyclohexylmethyl. Especially preferred are compounds wherein $R_3$ is phenyl, phenylmethyl, 1-naphthylmethyl or 2-naphthylmethyl.

The preferred compounds of formula (I) and (Ia) or (I') and (Ia') will also include a N-acyl group ($R_4$—C(O)—), at the N-terminus of the third amino acid analogue. Suitable $R_4$ groups include methyl, ethyl, 1,1-dimethylethyl, propyl, 2-methylpropyl, 2,2-dimethylpropyl, butyl, pentyl, hexyl, cyclopentyl, cyclopentylmethyl, cyclohexyl, cyclohexylmethyl, adamantyl, adamantylmethyl, 2-propenyl, 3-butenyl, 1-pentenyl, 2-pentenyl, 5-hexenyl, 2-cyclopentenyl, phenyl, phenylmethyl, diphenylmethyl, biphenyl, biphenylmethyl, naphthyl, naphthylmethyl, 1,1-dimethylethyloxy, 2-methylpropyloxy, 2,2-dimethylpropyloxy, cyclopentyloxy, cyclopentylmethyloxy, cyclohexyloxy, cyclohexylmethyloxy, adamantyloxy, adamantylmethoxy, phenoxy, benzyloxy, biphenylmethyloxy, naphthloxy, naphthylmethyloxy, or 2-carboxyethyl. Especially preferred are compounds wherein $R_4$ is methyl or 1,1-dimethylethyloxy.

Preferred peptide aldehydes of the present invention include:

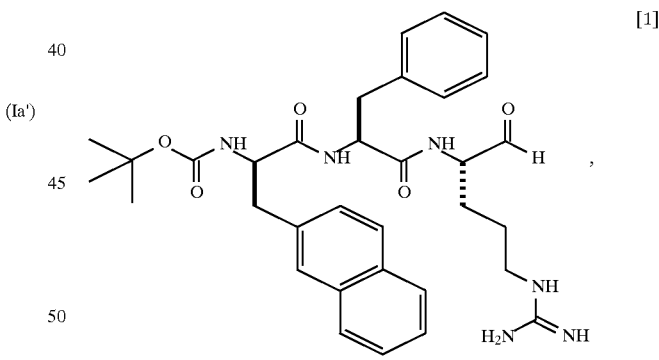

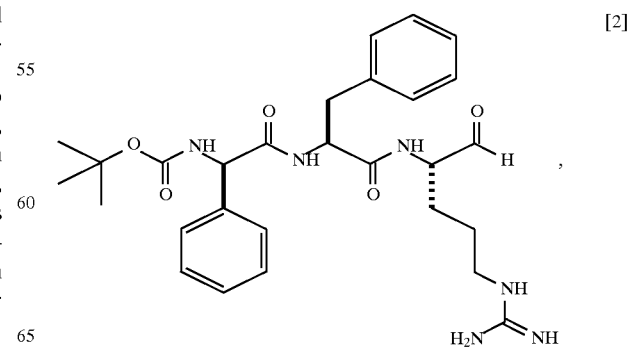

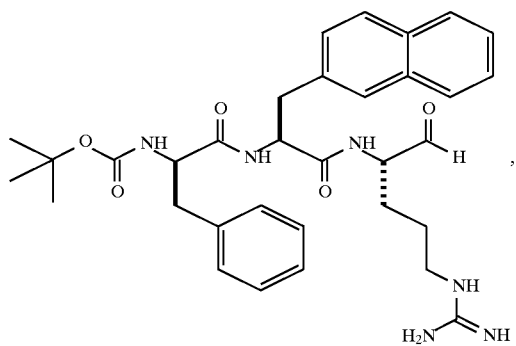
[3]
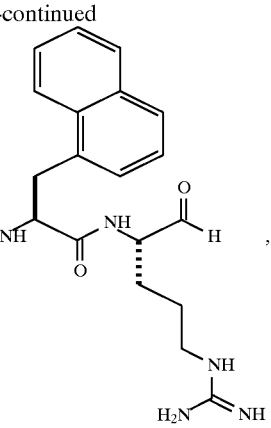
[7]
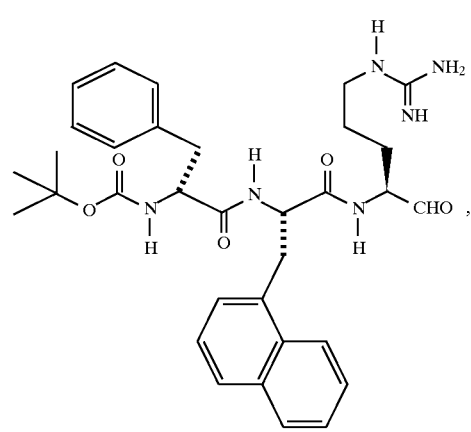
[4]
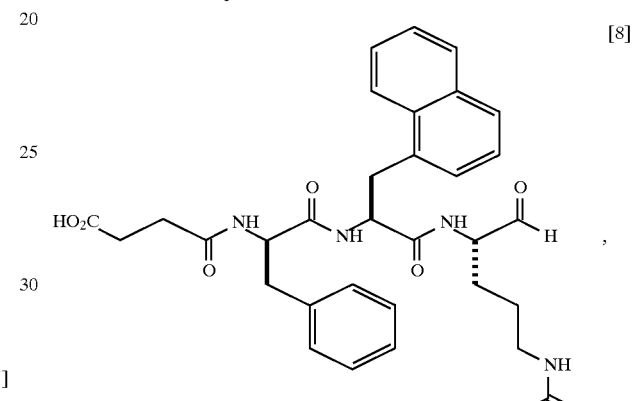
[8]
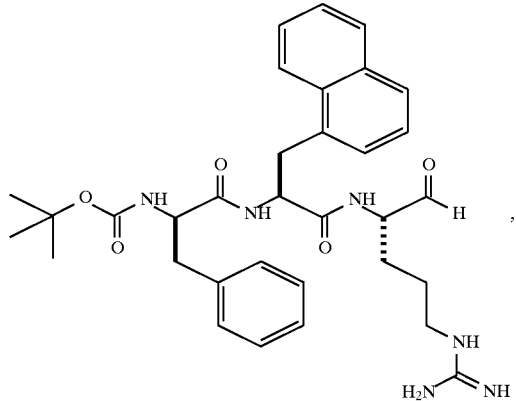
[5]
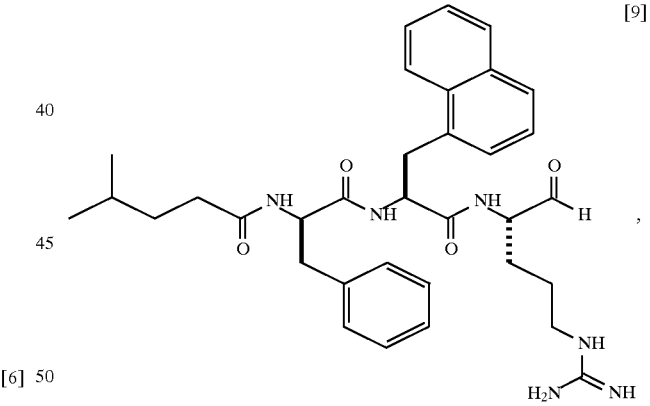
[9]
and
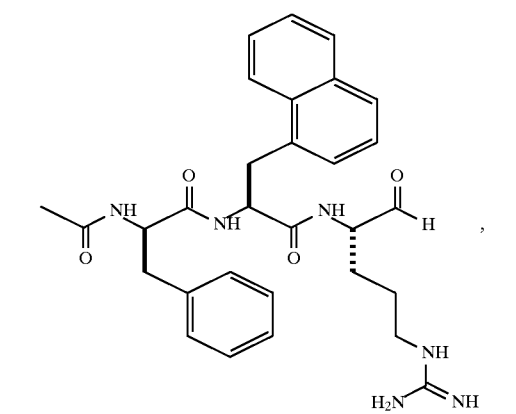
[6]
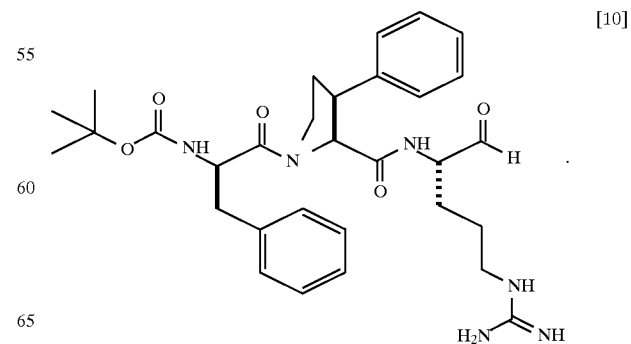
[10]

Another aspect of the present invention is directed to intermediates useful for the preparation of the novel N-acyl peptide aldehyde derivatives of formulas (I) and (I'). These intermediates are depicted by the formulas (II) and (II') below:

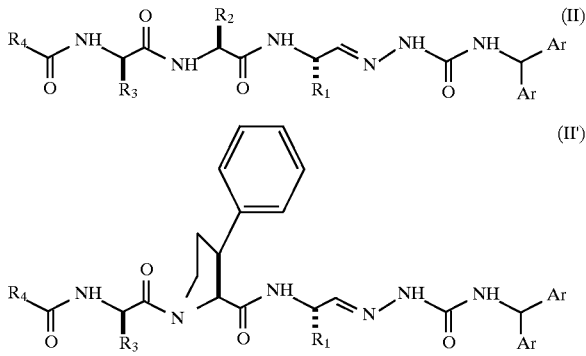

wherein $R_1$, $R_2$, $R_3$ and $R_4$ are as defined in connection with formulas (I) and (I') and Ar is an aryl group.

Preferred intermediates include those wherein Ar has the formula:

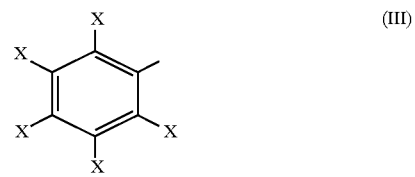

where each X is independently selected from the group consisting of hydrogen, methyl, halogen, and ethyl. Especially preferred are intermediates where Ar is phenyl.

Preferred intermediates of formulas (II) and (II') include compounds wherein $R_1$ is —$(CH_2)_3$—NH—C(=$NNO_2$)—$NH_2$.

Preferred groups for $R_2$, $R_3$ and $R_4$ are the same as those given for formulas (I) and (I') hereinabove. Especially preferred intermediates include those where $R_2$ is phenylmethyl, 1-naphthylmethyl or 2-naphthylmethyl; $R_3$ is phenyl, phenylmethyl, 1-naphthylmethyl or 2-naphthylmethyl; and $R_4$ is methyl or 1,1-dimethylethyloxy.

Particularly preferred intermediates of the present invention include:

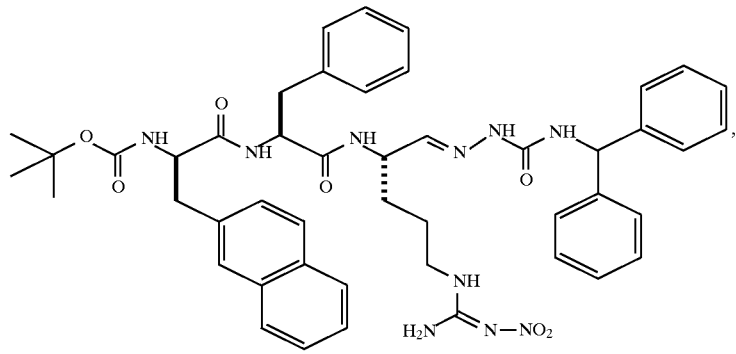

[11]

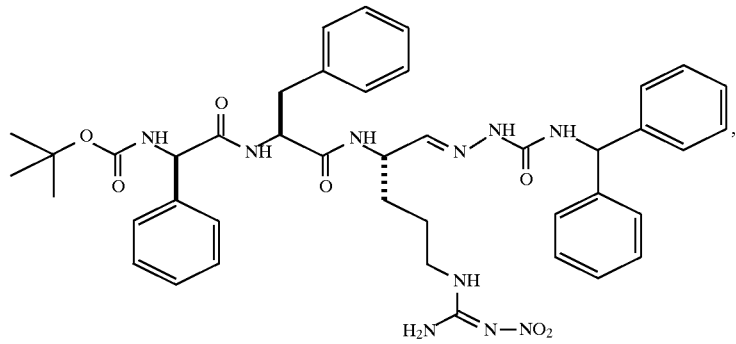

[12]

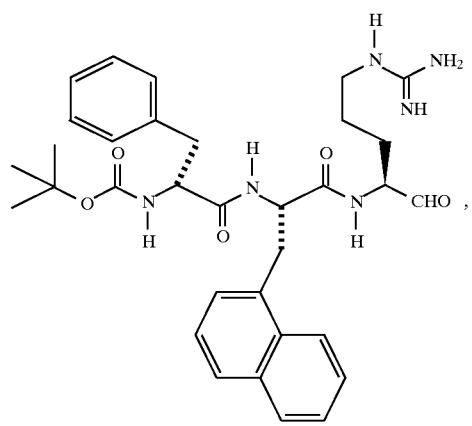
[13]
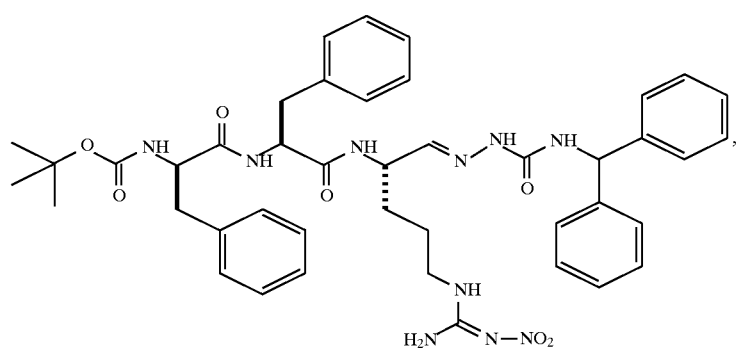
[14]
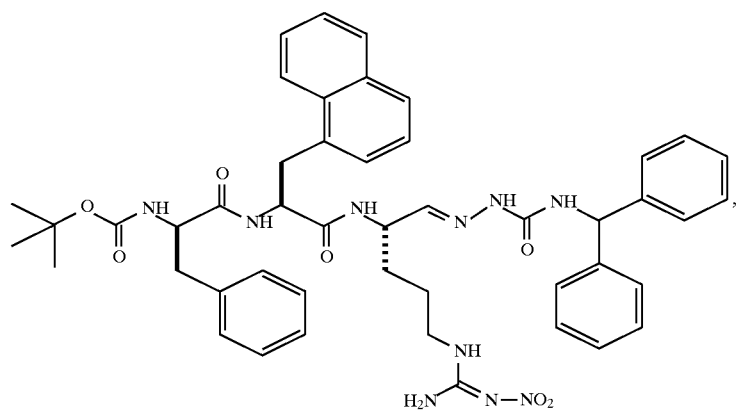
[15]
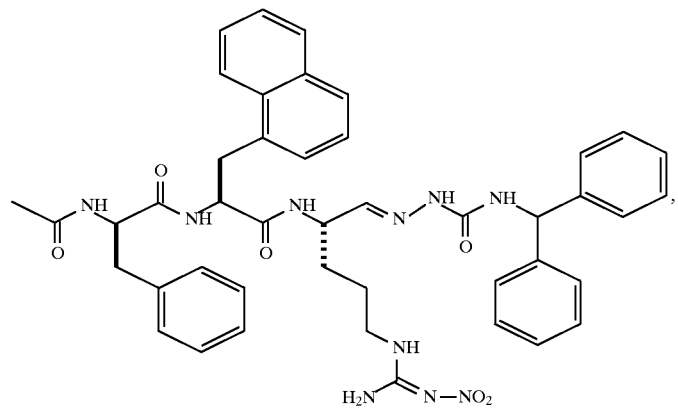
[16]

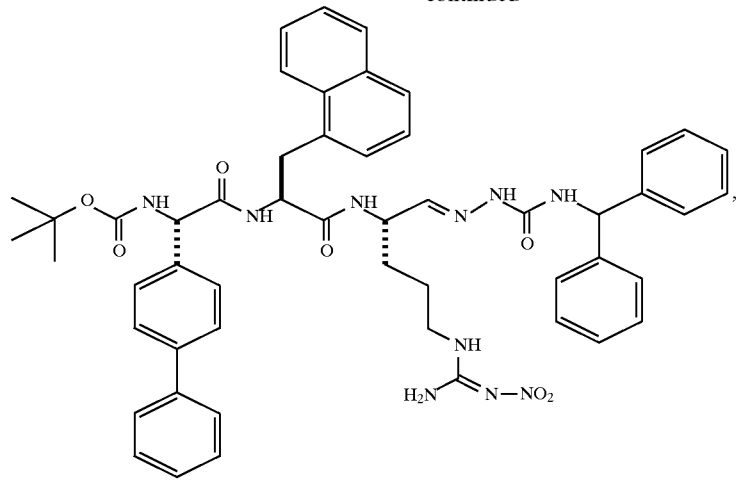
[17]
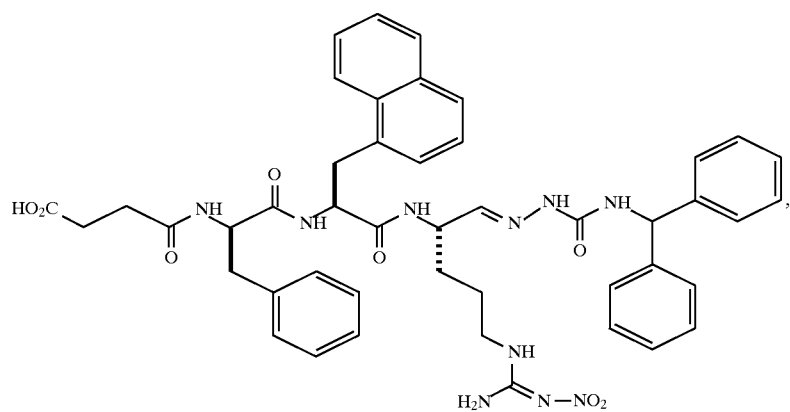
[18]
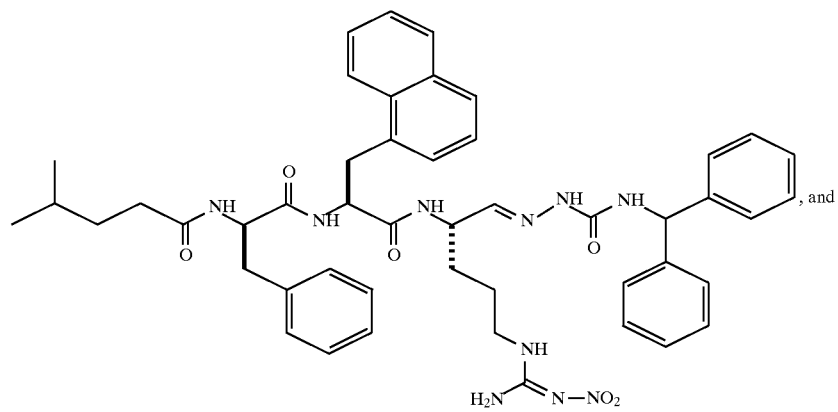
[19]
, and
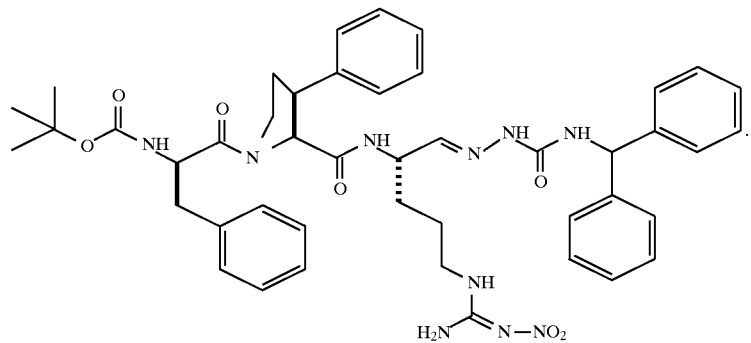
[20]

Preparation of Preferred Compounds

The peptide aldehyde derivatives of the present invention may be synthesized by either solid or liquid phase methods. Under certain conditions, such as large scale syntheses, the liquid phase method described herein is preferred.

Starting materials used in the preparation of these compounds by either method are readily available from commercial sources as Aldrich, Bachem BioScience Inc., Nova Biochemicals, Sigma and the like.

During the synthesis of these compounds, the functional groups of the amino acid derivatives used in these methods are protected by blocking groups to prevent cross reaction during the coupling procedure. Examples of suitable blocking groups and their use in peptide synthesis are described in "The Peptides: Analysis, Synthesis, Biology", Academic Press, Vol. 3 (E. Gross & Meienhofer edit. 1981) and Vol. 9 (S. Udenfriend & J. Meienhofer edit. 1987), the disclosures of which are incorporated herein by reference.

The peptide aldehyde derivatives of the present invention may be synthesized by procedures described in the literature (see below) or by sequential chemical attachment of amino acid derivatives using the solid phase synthesis reagents and methods described in the commonly assigned U.S. patent application of Webb, Ser. No. 07/807,474, filed Dec. 13, 1991, the disclosure of which is incorporated herein by reference.

FIG. 1 herein illustrates the synthesis of a solid phase reagent to which amino acid derivatives may be later attached in the solid phase synthesis method.

Figure 2:
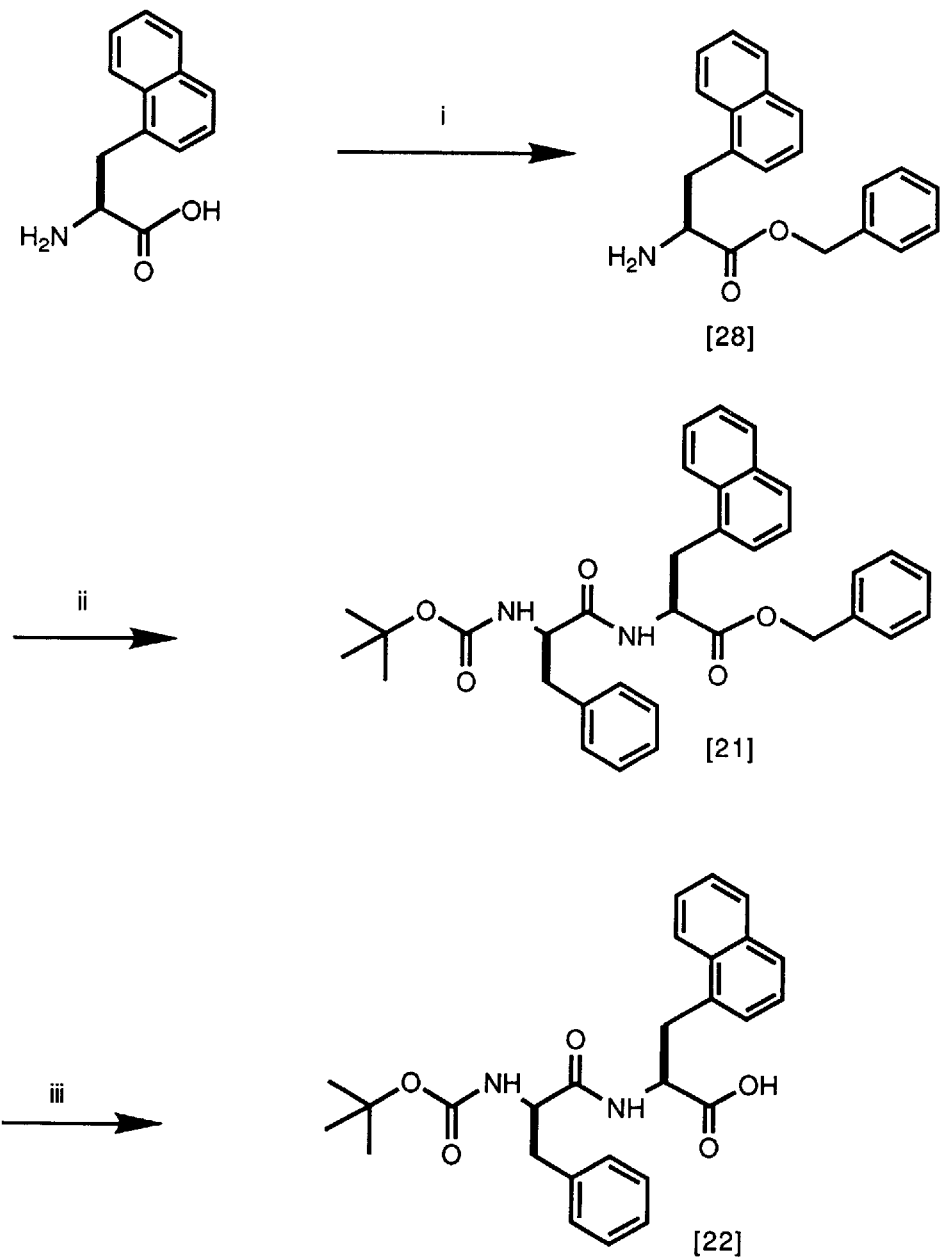
FIG. 2 depicts a reaction scheme describing a process for synthesis of compound which may subsequently be used to make one or more of the compounds of the present invention. In this figure, i represents p-toulenesulfonic acid and benzyl alcohol; ii represents Boc-D-phenylalanine, BOP and NMM in DMF; and iii represents hydrogen gas at 30 psig with 10% palladium on carbon in THF.
Figure 3:
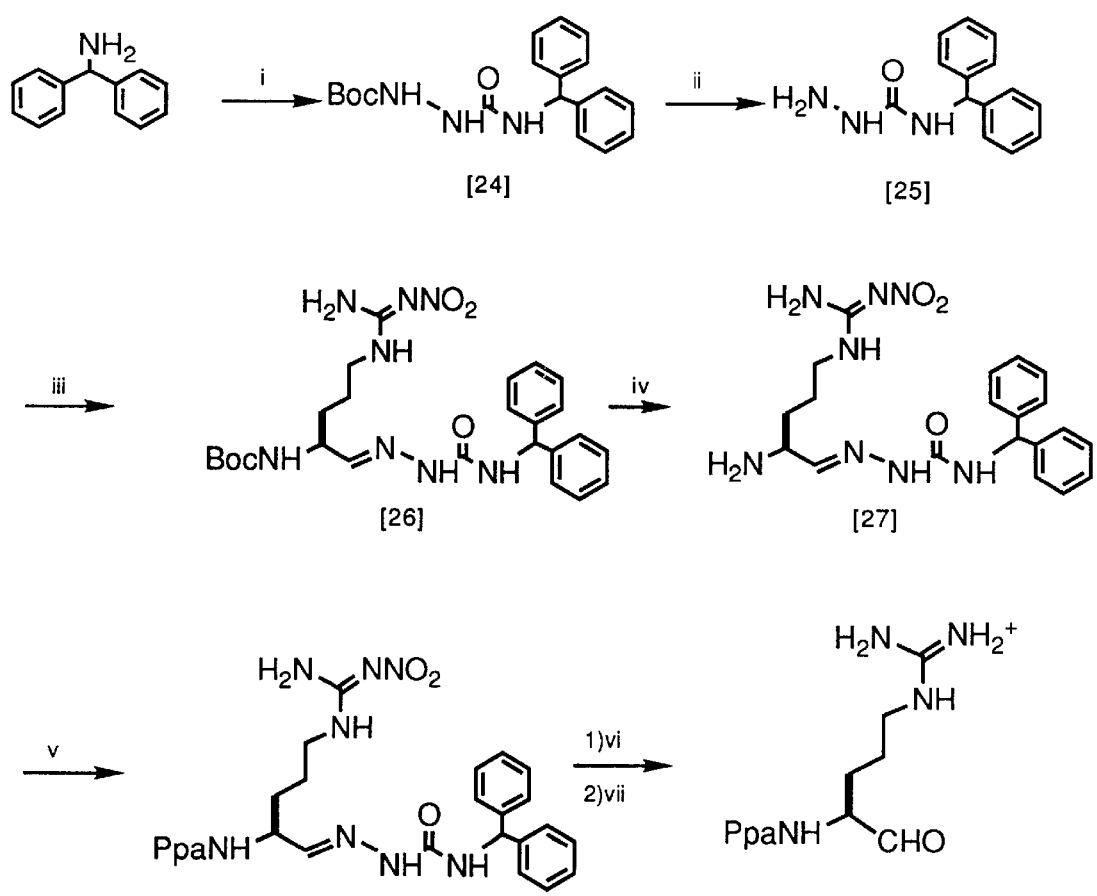
FIG. 3 depicts a reaction scheme describing a process for synthesis of one compound of the present invention using a liquid-phase method. In this figure, i represents t-butylcarbazate and carbonyldiimidazole in DMF under nitrogen; ii represents trifluoroacetic acid at 0° C.; iii represents compound 1 with sodium acetate in refluxing ethanol/water; iv represents trifluoroacetic acid in dichloromethane at 0° C.; v represents a protected peptide analog ("Ppa") such as compound [22] with BOP and NMM in DMF; vi represents hydrogen gas at 15 psig with 10% palladium on carbon in acidified methanol/acetic acid or HF/anisole followed by vii; and vii represents formaldehyde in acidified methanol/acetic acid.

The peptide aldehyde derivatives of the present invention may also be synthesized by solution phase methods. Preferred is the method depicted in FIGS. 2 and 3. FIG. 2 depicts a process for the synthesis of a compound subsequently used to prepare the compounds of the present invention. FIG. 3 depicts a preferred process for the solution phase synthesis of the compounds of the present invention. Other methods for the solution synthesis of peptide aldehydes have been reported and may be used to prepare the compounds of formulas (I) and (I'). For example, see McConnell et al., J. Med. Chem., 33: 86, at 87 (1989) and references cited therein; Kawamura et al., Chem. Pharm. Bull., 17: 1902 (1969), and Someno et al., Chem. Pharm. Bull., 34: 1748 (1986).

The intermediates of the present invention, as depicted in formulas (II) and (II'), may be synthesized by the solution phase method shown in FIG. 3. This solution phase method of preparation of the intermediates is preferred.

Utility and Formulation

As discussed in the Background section, factor Xa catalyzes the formation of thrombin which is the penultimate reaction in the coagulation cascade common to both the intrinsic and extrinsic initiation pathways which terminate in the formation of a fibrin clot. Inhibitors of factor xa would therefore inhibit fibrin deposition, thrombus formation and the consumption of coagulation proteins. Accordingly, the compounds of the present invention are thought to be useful either as in vitro diagnostic reagents for selectively inhibiting in a sample factor xa without inhibiting factor XIa, thrombin or tissue plasminogen activator (tPA), or as pharmacological agents for preventing or treating certain thrombotic disorders.

The compounds of the present invention are distinguished by their specificity for factor Xa, that is, their ability to inhibit the catalytic activity of factor xa while not appreciably inhibting the catalytic activity of factor XIa, thrombin and tPA. This specificity of the described inhibitors of actor Xa is an important feature of the compounds of the present invention with respect to their ability to inhibit thrombus formation. The importance of specifically inhibiting factor xa versus thrombin as demonstrated by the compounds embodied in this application may be better understood if one considers the amplified nature of the coagulation cascade where one moledule of factor Xa can result in the generation of 200,000 thrombin molecules per minute. Therefore, the amount of a selective factor Xa inhibitor required to achieve a relevant in vitro or in vivo antithrombotic effect will be considerably less than a comparable thrombin inhibitor of equal potency or another inhibitor of thrombus formation which lacks this specificity.

The use of stoppered test tubes having vaccum therein as a means to draw blood obtained by venepuncture into the tube is well known in the medical arts. Kasten, B. L., "Specimen Collection", *Laboratory Test Handbood,* 2nd Edition, Lexi-Comp Inc., Cleveland pp. 16–17 (Edits. Jacobs, D. S. et al. 1990). Such vacuum tubes may be free of clot-inhibiting additives, in which case, they would be useful for the isolation of mammalian serum from the blood. They may alternatively contain clot-inhibiting additives (such as heparin salts, EDTA salts, citrate salts or oxalate salt), in which case, they would be useful for the isolation of mammalian plasma from the blood. The compounds of the present invention are thought useful as additives for incorporation into blood collection tubes to prevent clotting of the blood drawn into them. As such, the compounds of the present invention would be useful as in vitro diagnostic reagents.

Inhibitors of factor Xa would be useful pharmacological agents for the treatment of many thrombotic disorders including, myocardial infarction, unstable angina, disseminated intravascular coagulation and associated complications resulting from venous thrombosis. In addition, these inhibitors would be useful as adjunctive or conjunctive agents to prevent recurrent thrombosis following enzymatic thrombolysis and percutaneous transluminal angioplasty. Furthermore, specific inhibitors of factor Xa may be useful in the supression of metastatic migration of certain tumor types as described by Tuszynski, G. P. et. al., "Isolation and characterization of antistasin, an inhibitor of metastasis and coagulation", J. Biol. Chem., 262: 9718–9723 (1987) and Brankamp, R. G. et. al., "Ghilantens: anticoagulants, antimetastatic proteins from the South American leech Haementeria ghilianii", J. Lab Clin. Med., 115: 89–97 (1990).

The specificity of the described inhibitors of factor Xa is an important feature of the compounds of the present invention with respect to their ability to control pathogenic thrombosis formation with minimal effects of the hemostatic potential of the treated patient. This will result in a reduction in the incidence of associated bleeding complications during therapy. The specificity of the described factor Xa inhibitors versus tPA is absolutely required if these compounds are to be used conjunctively with this thrombolytic agent in the reperfusion of infarct-related coronary vessels. Overall, the more specificity the inhibitor exhibits towards individual enzymes in the coagulation cascade, the less probability exists that unwanted side effects will occur during therapy. Accordingly, the compounds of the present invention are thought useful as pharmacological agents for preventing or treating certain in vivo thrombotic disorders.

To assay their activities, the compounds of the present invention are dissolved in buffer to give solutions containing concentrations ranging under assay concentrations from 0 to about 100 $\mu$M. The enzyme to be tested is then added to a solution containing a specified concentration of the test compound. Then after an incubation period, synthetic substrate for the enzyme being tested is added. The rate of substrate turnover is determined spectrophotometrically. The $IC_{50}$ of the test compound is determined for each test compound in assays for factor xa, factor XIa, thrombin and tPA. $IC_{50}$ is that concentration of test compound giving 50% inhibition of the substrate turnover. Percent selectivity is used to indicate selectivity of a compound in inhibiting Factor Xa in comparison with either Factor XIa, thrombin or tPA. Percent selectivity of a particular compound for either Factor XIa, thrombin or tPA refers to a number obtained by dividing the product of one hundred and the $IC_{50}$ of the compound for Factor Xa by the $IC_{50}$ of the compound for either Factor XIa, thrombin or tPA.

Preferred are those compounds of formulas I and I' for which the percent Selectivity for factor XIa, thrombin and tPA are each less than or equal to 10. The Percent Selectivity of each inhibitor for factor Xa is taken as 100. A Percent Selectivity less than 100 for a given compound indicates it is a stronger inhibitor of Factor xa than of either of Factor XIa, thrombin or tPA. The smaller the percent selectivity, the less active that compound is for inhibition of factor XIa, thrombin or tPA.

The present invention provides compounds, their pharmaceutically acceptable salts and pharmaceutically acceptable compositions prepared from them which are thought useful as potent and specific inhibitors of factor Xa, both in vitro and in vivo. In mammals, the in vivo uses would include their administration as a therapeutic agent to prevent the formation of fibrin clots in blood vessels resulting from the presence of factor Xa, to prevent abnormal thrombus formation resulting from thrombotic disorders, and to prevent or treat the recurrent thrombus formation resulting from chemical or mechanical intervention directed to clearing blocked vessels. Additionally, the compounds, their salts and various compositions derived therefrom are thought useful as therapeutic agents for suppressing the metastatic migration of tumor types in mammals by virture of their inhibitory properties.

The present invention also encompasses the pharmaceutically acceptable salts of the compounds of formulas (I) and (I'). These salts include acid addition salts, for example, salts of hydrochloric acid, hydrobromic acid, acetic acid, benzene sulfonic acid and other suitable acid addition salts.

The present invention also encompasses compositions prepared for storage and subsequent administration which comprise a therapeutically effective amount of a compound of the present invention in a pharmaceutically acceptable carrier or diluent. Pharmaceutically acceptable carriers or diluents for therapeutic use are well known in the pharmaceutical art, and are described, for example, in *Remington's Pharmaceutical Sciences,* Mack Publishing Co. (A. R. Gennaro edit. 1985). Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

The compositions of the present invention may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxilliary substances, such as wetting agents, pH buffering agents, and the like. If desired, absorption enhancing preparations (e.g., liposomes) may be utilized.

The present invention also includes a method for preventing or treating a condition in mammals characterized by abnormal thrombosis. The therapeutically effective amount of the composition required as a dose will depend on the route of administration, the type of mammal being treated, and the physical characteristics of the specific mammal under consideration. The dose can be tailored to achieve optimal efficacy but will depend on such factors as weight, diet, concurrent medication and other factors which those skilled in the medical arts will recognize.

In practicing the methods of the invention, the compounds or compositions can be used alone or in combination with one another, or in combination with other therapeutic or diagnostic agents. These compounds can be utilized in vivo, ordinarily in a mammal, preferably in a human, or in vitro. In employing them in vivo, the compounds or compositions can be administered to the mammal in a variety of ways, including parenterally, intravenously, subcutaneously, intramuscularly, colonically, rectally, nasally or intraperitoneally, employing a variety of dosage forms.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, will be within the ambit of one skilled in the art. Typically, applications of compound are commenced at lower dosage levels, with dosage level being increased until the desired effect is achieved.

The dosage for the compounds of the present invention can range broadly depending upon the desired affects and the therapeutic indication. Typically, dosages will be between about 0.01 µg/kg and 100 mg/kg body weight, preferably between about 0.01 µg/kg and 10 mg/kg body weight. Administration is preferably parenteral, such as intravenous on a daily basis.

To assist in understanding the present invention, the following examples are included which describe the results of a series of experiments. The following examples relating to this invention should not, of course, be construed as specifically limiting the invention. Variations of the invention, now known or later developed, which would be within the purview of one skilled in the art are considered to fall within the scope of the invention as described herein and hereinafter claimed.

The invention will now be further illustrated by the following examples. The Examples 1 to 7 illustrate the reaction scheme of FIG. 1. Examples 18 through 20 illustrate the reaction scheme of FIG. 2. Examples 14 through 17, 21 and 22 illustrate the reaction scheme of FIG. 3.

EXAMPLES

Example 1

Preparation of α-N-t-butoxycarbonyl-N$^g$-nitroargininal

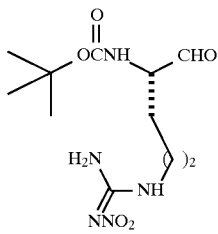

The following procedure for the synthesis of α-N-t-butoxy-carbonyl-N$^g$-nitro-argininal (1) is a modification of the procedure of Fehrentz, J. A. and Castro, B., Synthesis, 676 (1983).

Boc-N$^g$-nitroarginine was obtained from Calbiochem. N-methyl piperidine, N,O-dimethylhydroxylamine hydrochloride and isobutylchloroformate, and lithium aluminum hydride may be obtained from Aldrich Chemical Company, Inc. Dichloromethane, ethyl acetate, methanol and tetrahydrofuran may be obtained from Fisher Scientific Company.

N-methyl piperidine (11.4 mL, 90 mmole) was slowly added to a stirred suspension of N,O-dimethylhydroxylamine (8.42 g, 94 mmole) in 75 mL dichloromethane which had been cooled to about 0° C. The solution was allowed to stir for 20 minutes then was kept cold for use in the next step. In a separate flask, Boc-N$^g$-nitroarginine (30.0 g, 94 mmole) was dissolved by heating in about 1400 mL of tetrahydrofuran and cooled under nitrogen to 0° C. A mixture of N-methylpiperidine (11.4 mL, 90 mmole) and isobutylchloroformate (12.14 mL, 94 mmole) was added and the mixture stirred for 10 minutes. The free hydroxylamine prepared above was added all at once and the reaction mixture was allowed to warm to room temperature then stirred overnight.

The resulting precipitate was removed by filtration then washed with 200 mL of tetrahydrofuran. After concentrating the filtrates to about 150 mL under vacuum, 400 mL of ethyl acetate was added, followed by ice to cool the solution. The cooled solution was washed with two 75 mL portions of 0.2N hydrochloric acid, two 75 mL portions of 0.5N sodium hydroxide, one portion of 75 mL of brine, then dried over anhydrous magnesium sulfate. Upon concentration in vacuum, 22.7 g (70% yield) of solid Boc-Ng-nitroarginine N-methyl-O-methylcarboxamide was recovered. Thin layer chromatographic analysis in 9:1 dichloromethane/methanol (silica gel) showed one spot.

A flask was placed under a nitrogen atmosphere charged with 70 mL of 1N lithium aluminum hydride in tetrahydrofuran and 500 mL of dry tetrahydrofuran then cooled to −50° C. A solution containing Boc-Ng-nitroarginine N-methyl-O-methylcarboxamide (23 g, 66 mmole) in 50 mL dry tetrahydrofuran was slowly added while the temperature of the reaction mixture was maintained at −50° C. After allowing the reaction mixture to warm to 0° C. by removal of the cooling, it was recooled to −30° C., at which temperature, 100 mL (0.2 mole) of 2N potassium bisulfate was added with stirring over a 15 minute period. The reaction mixture was then allowed to stir at room temperature for 30 minutes. The resulting mixture was filtered and the filtrate was concentrated to 100 mL under vacuum. The concentrate was diluted with 800 mL ethyl acetate, then was washed with two 50 mL portions of 1N hydrochloric acid, two 50 mL portions of saturated sodium bicarbonate, and one 50 mL portion of brine. The combined aqueous extracts were extracted with three 100 mL portions of ethyl acetate. All of the ethyl acetate washes were combined, then dried over anhydrous magnesium sulfate. The mixture was concentrated under vacuum to yield 13.6 g (70%) of the titled compound.

Example 2

Preparation of trans-4-(aminomethyl)-cyclohexane carboxylic acid benzyl ester para-touluenesulfonate salt

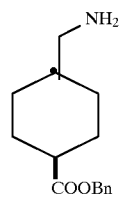

Trans-4-(aminomethyl)-cyclohexane carboxylic acid (50 g, 0.318 moles), p-toluenesulfonic acid monhydrate (61.7 g, 0.324 moles), benzyl alcohol (250 mL, 2.4 moles) and 250 mL of toluene were combined and stirred. The mixture was refluxed for 24 hours and the liberated water was removed by means of a Dean-Stark apparatus. A clear solution was obtained after 5 hours of refluxing. The solution was allowed to cool to room temperature whereupon the product crystallized. The mixture was vacuum filtered, washed with ether and dried in a vacuum oven to give 128.12 g (96% yield). Greenstein, J. P. and Winitz, M., "Chemistry of the Amino Acids", Robert E. Krieger Publishing Company, Malabar, Fla., Vol. 2, p942 (1986). $^1$H NMR (CD$_3$OD) δ 1.05 (m, 2H), 1.43 (m, 2H), 1.59 (m, 1H), 1.85 (m, 2H), 2.03 (m, 2H), 2.33 (m, 1H), 2.35 (s, 3H), 2.75 (d, 2H), 5.09 (s, 2H), 7.23 (d, 2H), 7.32 (m, 5H), 7.69 (d, 2H). M.P. 154°–156° C.

Example 3

Preparation of 1-t-butoxycarbonyl-semicarbazidyl-trans-4-methyl cyclohexane carboxylic acid benzyl ester

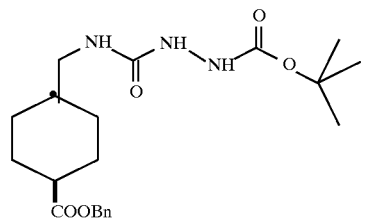

Carbonyldiimidazole (3.24 g, 0.02 moles) was dissolved in 45 mL of dimethylformamide (DMF) at room temperature under nitrogen. A solution of t-butyl carbazate (2.48 g, 0.02 moles) in 45 mL of DMF was added dropwise. The solid benzyl ester 2 (8.38 g, 0.02 moles) was then added, followed by the dropwise addition of 3.06 mL of triethylamine over a 30 minute period. The reaction was allowed to stir at room temperature under nitrogen for one hour. 100 mL of water was added and this mixture was extracted three times with 50 mL of ethyl acetate. The ethyl acetate layers were combined and extracted two times each with 75 mL of 1N hydrochloric, water, saturated sodium bicarbonate, brine and dried with anhydrous magnesium sulfate. The mixture was filtered and the solution was concentrated to give an oil. This material could be purified by recrystallization from ethyl acetate/hexanes (M.P.=106°–108° C.) or used directly in the next step. ¹H NMR (CDCl₃) δ 0.94 (m, 2H), 1.42 (m, 2H), 1.45 (S, 9H), 1.81 (m, 2H), 2.02 (m, 2H), 2.27 (m, 1H), 3.17 (t, 2H), 5.09 (S, 2H), 5.51 (t, 1H), 6.46 (S, 2H), 7.34 (m, 4H).

Example 4

Preparation of 1-(t-butoxycarbonyl)-3-semicarbazidyl-trans-4-methyl-cyclohexane carboxylic acid

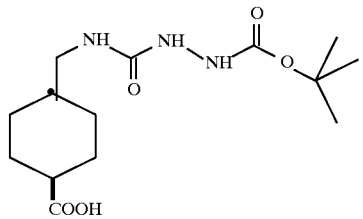

4

The crude Boc-benzyl ester 3 from above in 250 mL of methanol was combined with 500 mg of 10% palladium on activated carbon. After shaking on the hydrogenator for one hour at 5 psig, the mixture was filtered through a pad of diatomaceous earth in a fine fritted filter. The filtrate was concentrated to a foam, methylene chloride was added and a precipitate formed. The crystallized material was filtered and washed with ether. This yielded 4.0 g of crude product (12.7 mmoles; yield 62% overall yield from compound 2.) ¹H NMR (CD₃OD), δ 0.96, (m, 2H), 1.42 (m, 2H), 1.46 (s, 9H), 1.82 (m, 2H), 1.97 (m, 2H), 2.18 (m, 1H), 3.0 (t, 2H). M.P.=185°–189° C.

Example 5

Preparation of semicarbazidyl-trans-4-methyl cyclohexane carboxylic acid trifluoroacetate salt

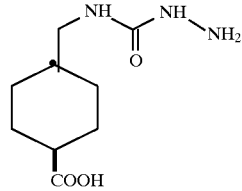

5

Compound 4 (315 mg, 1 mmole) was added to 10 mL of trifluoroacetic acid at 0° C. and the resulting solution was allowed to stir for 30 minutes. After this time the solution was added dropwise to 75 mL of dry ether. A precipitate formed, and the mixture was filtered and washed with ether. Weight of crude product was 254 mg (77% yield). ¹H NMR (CD₃OD), δ 1.0 (m, 2H), 1.38 (m, 2H), 1.43 (m, 1H), 1.84 (m, 2H), 2.01 (m, 2H), 2.22 (m, 1H), 3.04 (d, 2H). M.P.= 154°–156° C.

Example 6

Preparation of a-(t-butoxycarbonyl)-N^g-nitro argininal-semicarbazonyl-trans-4-methyl-cyclohexane carboxylic acid

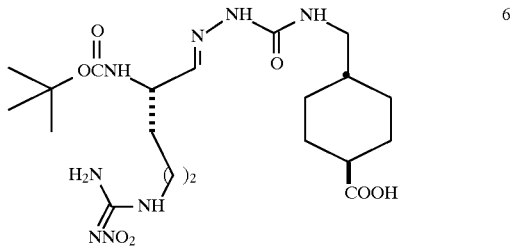

6

A solution of 5 (13.7 g, 41.6 mmoles) and crude 1 (18.0 g, 59 mmoles) in 135 mL of ethanol, containing 45 mL of water, was treated with sodium acetate trihydrate (9.41 g, 69 mmole) and refluxed for one hour. This solution was allowed to cool and then poured into 0.1N hydrochloric acid and extracted with three times using 100 mL of ethyl acetate per extraction. The combined organic phases were washed with water, brine, dried over anhydrous magnesium sulfate and concentrated to a small volume. This cloudy mixture was allowed to set overnight at 5° C. to precipitate the product, which was isolated by filtration and dried under vacuum. This gave 9.9 g, 47% yield based on 5. ¹H NMR (CD₃OD), δ 1.0 (m, 2H), 1.43 (s, 9H), 1.45–2.20 (m, 13H), 3.09 (d, 2H), 3.30 (m, 2H), 4.18 (bs, 1H), 7.10 (d, 1H). M.P.= 162°–163° C.

Example 7

Synthesis of Semicarbazone Solid Support

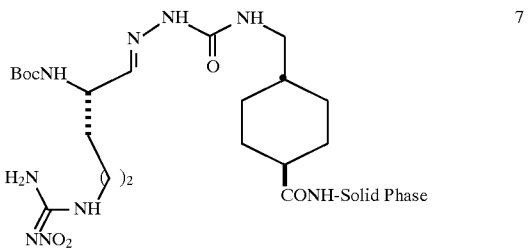

7

Solid phase reagent 7 was prepared by placing methylbenzhydralamine (MBHA) (0.8 g, 0.5 mmoles, 0.62 g/mole) resin in a reaction vessel and washing one time with dichloromethane (DCM) (all washes require 10 mL of solvent with agitation for 1 to 2 minutes), three times with dimethylformamide (DMF), two times with 10% diisopropylethylamine (DIEA)/DMF, and four times with DMF. 5 mL of DMF, 4-methylmorpholine (102 μL, 1 mmole), benzotriazol-1-yloxy-tris-(dimethylamino)-phosphonium-hexafluorophosphate (BOP reagent, 443 mg, 1 mmole) and compound 6 (500 mg, 1 mmole) were added, mixed on a rotating wheel for 16 hours, and washed three times with DMF, two times with 10% DIEA/DMF and three times with DMF. The resin was then washed successively with DCM, methanol and ether. The resulting resin 7 showed a 98–99% coupling yield by ninhydrin.

This resin was then extended at the N-terminus, with amino acids or amino acid analogs, on a conventional peptide synthesizer using standard t-Boc methodology as shown in the examples which follow.

The synthesis of the peptide analogs was performed on an Applied Biosystems Model 430A peptide synthesizer using the t-Boc chemistry conditions in the 430A user's manual. The resulting protected peptide aldehyde can be cleaved from the support with a mixture of aqueous acid and formaldehyde, and then deprotected with hydrogen/Pd. The nitro group can be removed from the guanidine group without reduction of the aldehyde.

Example 8

Preparation of N-t-butoxycarbonyl-D-3-(2-naphthyl) alanyl-L-phenylalanyl-L-araininal

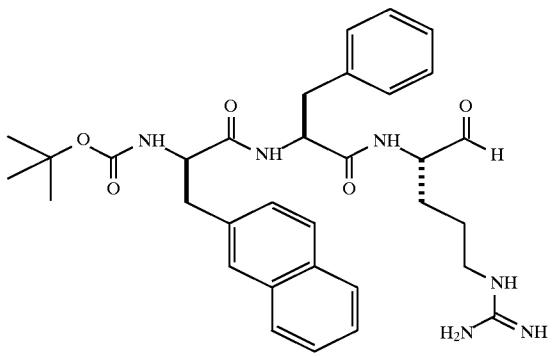

[1]

The above peptide aldehyde was synthesized using an Applied Biosystems Model 430A peptide synthesizer. The Boc chemistry conditions utilized were as provided in the instrument user's manual.

Resin 7 (1.00 g, 0.500 mmole) was made ready for use by removing the Boc protecting groups by treatment with 50% trifluoroacetic acid (in dichloromethane). After washing and neutralizing the acidity by treatment with 10% diisopropylethylamine (in dichloromethane), commercially available Boc-protected amino acids were coupled to the support reagent (and the growing amino acid support chain) in a sequential manner.

Thus, N-Boc-L-phenylalanine was attached to the resin using dicyclohexylcarbodiimide and 1-hydroxybenztriazole in dimethylformamide, followed by treatment with 50% trifluoroacetic acid (in dichloromethane) to remove the Boc protecting group, a wash step and a wash with 10% diisopropylethylamine (in dichloromethane) to neutralize acidity. N-Boc-D-3-(2-naphthyl)alanine was coupled in the same manner. The treatement with 50% trifluoroacetic acid was omitted after the last coupling.

The peptide aldehyde was removed from the solid phase, by treatment with a mixture comprising 5 mL of tetrahydrofuran, 1 mL of acetic acid, 1 mL of formaldehyde and 0.100 mL of 1N hydrochloric acid for 1 hour with stirring. After filtering this mixture, the resin was washed with 10 mL of tetrahydrofuran. The combined filtrates were diluted with 100 mL water and extracted with ethyl acetate. The ethyl acetate phase was then washed with saturated sodium chloride, dried over magnesium sulfate, and concentrated under vacuum.

To remove the nitro and benzyl (where applicable) protecting groups of the peptide aldehyde, the concentrated peptide aldehyde was taken up in a mixture 10 mL of 10% water in methanol, 0.300 mL of 1N hydrochloric acid and 0.200 g of palladium on carbon, then treated with hydrogen at 5 psig for 45 minutes. The mixture was filtered through a fine fritted filter with diatomaceous earth, washed with 10% water in methanol and concentrated to give the crude peptide aldehyde.

The resulting peptide aldehyde is then purified using reverse phase HPLC on a 10 micron particle size, 300 angstrom pore size C-18 column, eluting with a water-acetonitrile (both containing 0.1% trifluoroacetic acid) gradient, where the gradient ran from 5% to 40% acetonitrile. The column fractions were analyzed by analytical HPLC and fractions containing pure product were pooled and lyophilized to yield the above-identified product. Fast atom bombardment mass spectrometry gave observed molecular weight of 602.5 a.m.u.; calculated molecular weight was 602.3 a.m.u.

Example 9

Preparation of N-t-butoxycarbonyl-D-2-phenylglycyl-L-phenylalanyl-L-araininal

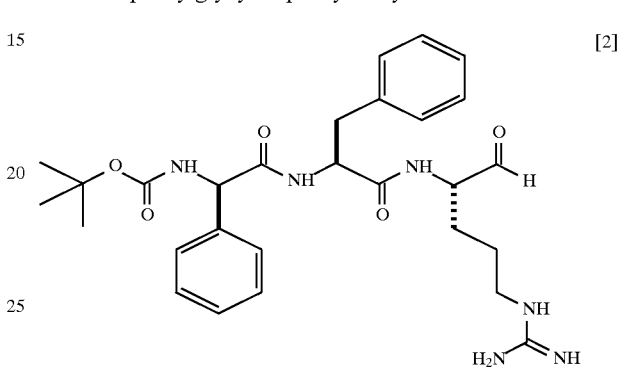

[2]

The above peptide aldehyde was synthesized and purified in the same manner as described in Example 8. Here, N-Boc-L-phenylalanine was first attached to resin 7 followed by N-Boc-D-phenylglycine. As in Example 8, the treatment with 50% trifluoroacetic acid was omitted after the last coupling step. Fast atom bombardment mass spectrometry gave an observed molecular weight of 538.3 a.m.u; calculated molecular weight was 538.3 a.m.u.

Example 10

Preparation of N-t-butoxycarbonyl-D-phenylalanyl-L-3-(2-naphthyl)alanyl-L-argininal

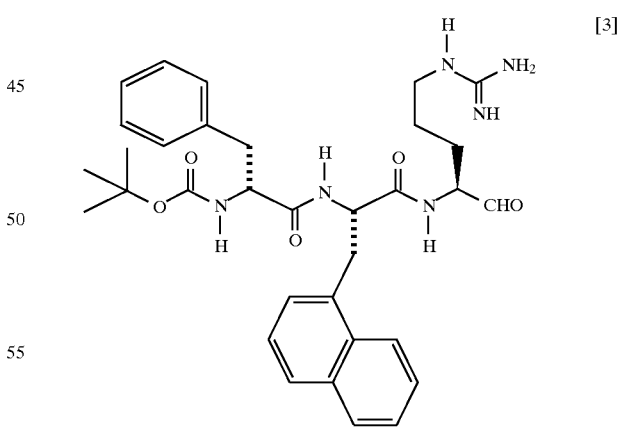

[3]

The above peptide aldehyde was synthesized and purified in the same manner as described in Example 8. Here, N-Boc-L-3-(2-naphthyl)alanine was first attached to resin 7, followed by N-Boc-D-phenylalanine. As in Example 8, the treatment with 50% trifluoroacetic acid was omitted after the last coupling step. Fast atom bombardment mass spectrometry gave an observed molecular weight of 602.3 a.m.u; calculated molecular weight was 602.3 a.m.u.

Example 11

Preparation of N-t-butoxycarbonyl-D-phenylalanyl-L-phenylalanyl-L-argininal

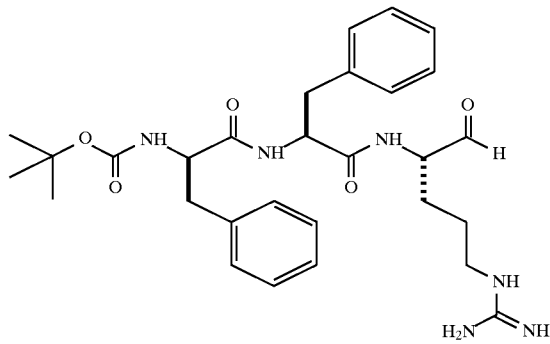

[4]

The above peptide aldehyde was synthesized and purified in the same manner as described in Example 8. Here, N-Boc-L-phenylalanine was first attached to resin 7 followed by N-Boc-D-phenylalanine. As in Example 8, the treatment with 50% trifluoroacetic acid was omitted after the last coupling step. Fast atom bombardment mass spectrometry gave an observed molecular weight of 552.5 a.m.u; calculated molecular weight was 552.6 a.m.u.

Example 12

Preparation of N-t-butoxycarbonyl-D-phenylalanyl-L-3-(1-naphthyl)alanyl-L-argininal

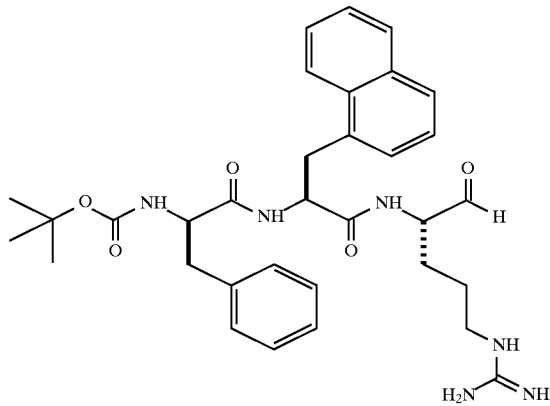

[5]

The above peptide aldehyde was synthesized and purified in the same manner as described in Example 8. Here, N-Boc-L-3-(1-naphthyl)alanine was first attached to resin 7 followed by N-Boc-D-phenylalanine. As in Example 8, the treatment with 50% trifluoroacetic acid was omitted after the last coupling step. Fast atom bombardment mass spectrometry gave an observed molecular weight of 602.4 a.m.u; calculated molecular weight was 602.7 a.m.u.

Example 13

Preparation of N-acetyl-D-phenylalanyl-L-3-(1-naphthyl)alanyl-L-argininal

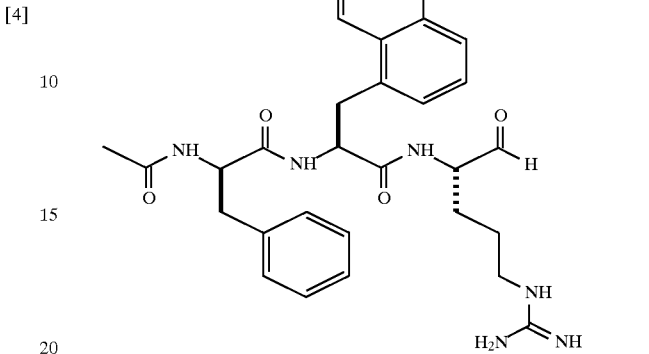

[6]

The above peptide aldehyde was synthesized and purified in the same manner as described in Example 8. Here, N-Boc-L-3-(1-naphthyl)alanine was first attached to resin 7 followed by N-acetyl-D-phenylalanine. As in Example 8, the treatment with 50% trifluoroacetic acid was omitted after the last coupling step. Fast atom bombardment mass spectrometry gave an observed molecular weight of 544.3 a.m.u; calculated molecular weight was 544.3 a.m.u.

Example 14

Preparation of 1-t-butoxycarbonyl-semicarbazidyl-4-diphenylmethane

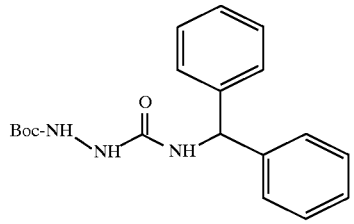

[24]

A solution of carbonyldiimidazole (16.2 g, 0.10 mole) in dimethylformamide (DMF, 225 mL) was prepared at room temperature and allowed to stir under nitrogen. A solution of t-butyl carbazate (13.2 g, 0.10 mole) in DMF (225 mL) was then added dropwise over a 30 minute. period. Next, diphenylmethylamine (18.3 g, 0.10 moles) in DMF (100 mL) was added over a 30 minute period. The reaction was allowed to stir at room temperature under nitrogen for one hour. Water (10 mL) was added and this mixture was concentrated to about 150 mL under vacuum. This solution was poured into water (500mL) and extracted with ethyl acetate (400 mL). The ethyl acetate phase was extracted two times each with 75 mL 1N hydrochloric acid, water, saturated sodium bicarbonate, brine and dried with anhydrous magnesium sulfate. The mixture was filtered and the solution was concentrated to give 29.5 g (85% yield) of a white foam. This material could be purified by recrystallization from ethyl acetate/hexane, but was pure enough to use directly in the next step: M.P.=142°–143° C. Anal. Calcd. for $C_{19}H_{23}N_3O_3$: C, 66.84; H, 6.79; N, 12.31. Found: C, 66.46; H, 6.75; N; 12.90.

Example 15

Preparation of semicarbazidyl-4-diphenylmethane trifluoroacetate salt

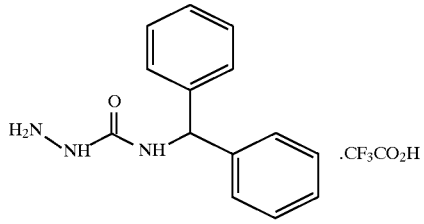

[25]

A solution of compound [24] (3.43 g, 10 mmole) in dichlormethane (12.5 mL) and trifluoroacetic acid (12.5 mL) was stirred at room temperature for 30 minutes. After this time the solution was added dropwise to ether (75 mL). A precipitate formed, and the mixture was filtered and washed with ether. Weight of crude product was 2.7 g (80% yield): mp 182°–184° C.

Example 16

Preparation of α-N-(t-butoxycarbonyl)-$N^g$-nitro-argininal-semicarbazonyl-4-N-diphenylmethane

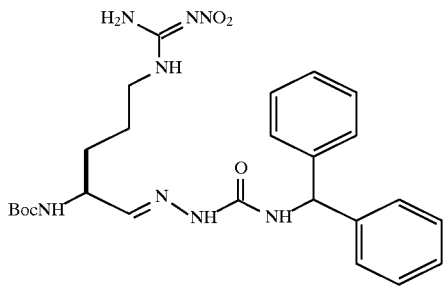

[26]

A solution of compound [25] (2.65 g, 7.8 mmoles) and 1 (α-N-(t-butoxycarbonyl)-$N^g$-nitro-argininal, 2.36 g, 7.8 mmoles) in ethanol (20 mL) containing water (20 mL) was treated with sodium acetate trihydrate (1.2 g, 8.8 mmoles) and refluxed for one hour. This solution was allowed to cool and then poured into water and extracted three times with ethyl acetate. The combined organic phase was washed with water, 0.1N hydrochloric acid, brine, dried with anhydrous magnesium sulfate, and concentrated to a small volume. The white solid residue was recrystallized from acetonitrile/ether. This gave 3.2 g (78% yield based on compound of Example 1: M.P.=78°–79° C.

Example 17

Preparation of $N^g$-nitro-argininal-semicarbazonyl-4-N-diphenylmethane trifluoroacetate salt

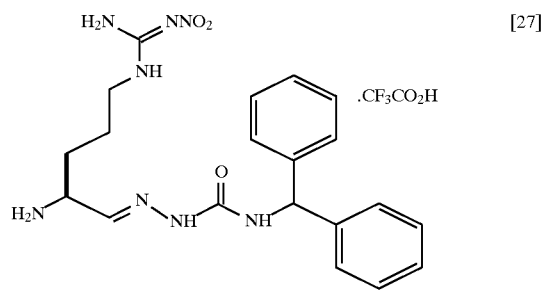

[27]

A solution of compound [26] (1.2 g, 8.8 mmoles) in dichloromethane (5 mL) and trifluoroacetic acid (5 mL) at room temperature was allowed to stir for 30 minutes. After this time, the solution was added dropwise to ether (40 mL). A precipitate formed, and the mixture was filtered and washed with ether. This gave 0.51 g of a pure white solid salt (97% yield): M.P.=159°–160° C.

Example 18

Preparation of L-3-(1-naphthyl)alanine-O-benzyl ester p-toluenesulfonic acid salt

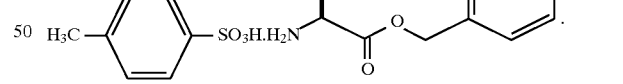

[28]

L-3-(1-naphthyl)alanine (25.0 g, 115 mmole), p-toluenesulfonic acid monohydrate (24.1 g, 127 mmole), toluene (1250 mL) and benzyl alcohol (29.8 mL, 288 mmole) were combined and refluxed with stirring overnight. Water (4.1 mL) was removed by a Dean-Stark trap. After cooling to room temperature, the resulting suspension was poured into 1000 mL of ether and stirred for 10 minutes. The solid was then filtered, washed with 1000 mL of ether and dried under vaccum to give 50.5 g (92% yield) of the title compound. M.P.=161°–163° C.

Example 19

Preparation of α-N-(t-butoxycarbonyl)-D-phenylalanyl-L-3-(1-naphthyl)alanine-O-benzyl ester

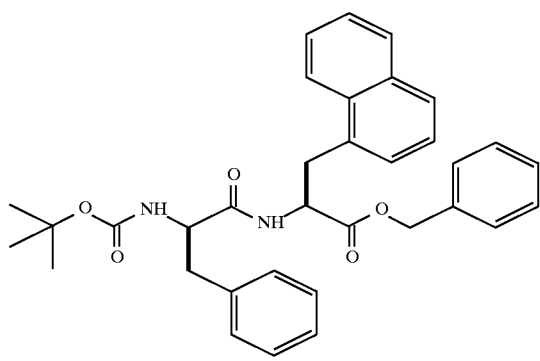

[21]

A solution of compound [28] (48.5 g, 101 mmole), Boc-D-phenylalanine (26.7g, 101 mmole) and benzotriazol-1-yloxy-tris-(dimethylamino)-phosphonium-hexafluorophosphate (BOP, 44.7 g, 101 mmole) was prepared in 240 ML of DMF. The reaction mixture was cooled to 0° C., then 33.3 mL of 4-methylmorpholine (NMM) was added with stirring. After stirring overnight, the reaction mixture was added to 800 mL of water and then extracted with two 400 mL portions of ethyl acetate. The organic layer was washed with an equal volume of 1N citric acid, water, saturated sodium chloride, and then was dried over anhydrous magnesium sulfate. The organic layer was concentrated under vacuum to give a solid. The solid was then recrystallized from ethyl acetate/hexanes to give 42 g (76% yield) of the pure crystalline title compound. M.P.=151°–153° C.

Example 20

Preparation of α-N-(t-butoxycarbonyl)-D-phenylalanyl-L-3-(1-naphthyl)alanine

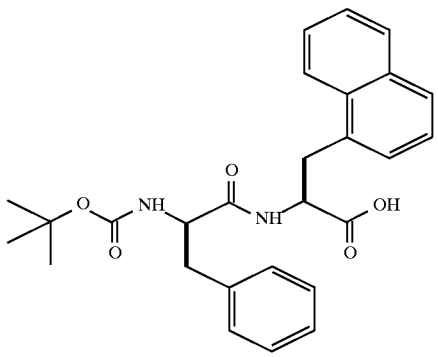

[22]

A solution of compound [21] (38 g, 69 mmole) in 1000 mL of tetrahydrofuran was placed in a Parr apparatus. The reaction mixture was purged of air with nitrogen gas for 30 minutes, then 38 g of 10% palladium on carbon which had been pre-moistened with 10 mL of water was added. After purging, the mixture was stirred for 2 hours at room temperature under 30 psig of hydrogen gas. After this time, the mixture was filtered. The filtrate was concentrated to dryness under vacuum to yield 28 g (88% yield) of the title compound. M.P.=113°–115° C.

Example 21

Preparation of α-N-(t-butoxycarbonyl)-D-phenylalanyl-L-3-(1-naphthyl)alanyl-L-Ng-nitro-argininal-semicarbazon yl-4-N-diphenylmethane

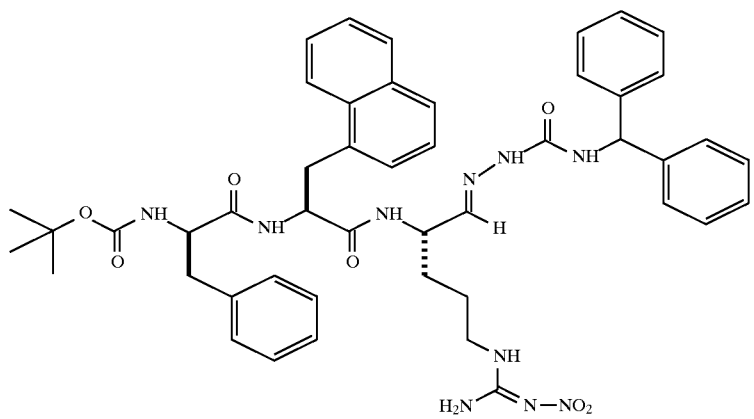

[15]

A solution of compound [27] (9.08 g, 16.7 mmole), compound [22] (7.72 g, 16.7 mmole), BOP (7.38 g. 16.7 mmole), NMM (5.27 mL, 48 mmole) and 50 mL of DMF was prepared and cooled to 0° C. The reaction mixture was stirred for 2 hours at this temperature. After this time, the reaction mixture was poured into 500 mL of ethyl acetate. 150 mL of water was added and this mixture was stirred for 20 minutes at room temperature. After this time, the stirring was discontinued and the layers separated. The organic layer was separated, then washed with an equal volume of saturated citric acid, saturated sodium bicarbonate, water and saturated sodium chloride, then was dried over anhydrous magnesium sulfate. After concentrating the organic layer to dryness, the crude product was redissolved in dichloromethane, then was chromatographed on a silica gel column, eluting with 4 to 16% isopropyl alcohol (in dichloromethane). The product eluted between 10 to 14% isopropyl alcohol (in dichloromethane). Fractions containing pure product were selected by use of thin-layer chromatography on silica gel, developing with 10% methanol in dichloromethane and pooled. The pool was reduced to dryness under vacuum to give 7 g (46% yield) of the title compound. M.P.=140°–150° C. (decomposed).

Example 22

Preparation of N-t-butoxycarbonyl-D-phenylalanyl-L-3-(1-naphthyl)alanyl-L-argininal

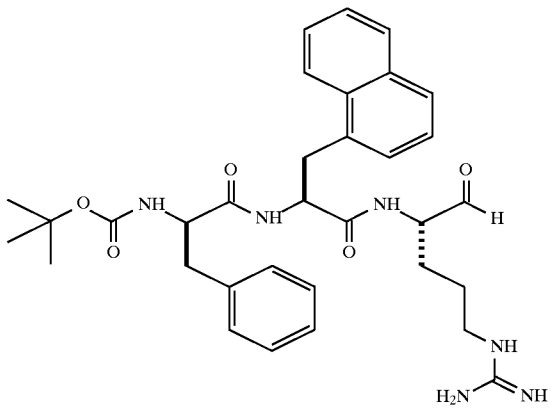

[5]

A solution of compound [15] (1.95 g, 2.15 mmole) and 98 mL of methanol was placed in a Parr vessel. 1M hydrochloric acid (3.9 mL), acetic acid (9.8 mL) and 10% palladium on carbon (1.95 g) pre-moistened with several drops of water were added, then the reaction mixture was purged of air with nitrogen gas for 30 minutes. After purging, the mixture, it was allowed to stir for 18 hours at room temperature under a 15 psig atmosphere of hydrogen gas. After this time, the palladium on carbon was filtered off and the filtrate was concentrated under vacuum to yield an oil.

The oil was redissolved in a solution comprised of 78 mL of methanol, 11 mL acetic acid, 0.6 mL of 1M hydrochloric acid and 6 mL of 37% formaldehyde (by weight in water), then allowed to stir for 45 minutes at room temperature. After this time, 200 mL of water was added and the solution was concentrated to about 200 mL under vacuum. 86 mL of acetonitrile was added to the cloudy concentrate to yield a clarified solution. The title compound was purified from the solution using reverse phase preparative HPLC on a 10 micron particle size, 300 angstrom pore size C-18 column, eluting with a water-acetonitrile (both containing 0.1% trifluoroacetic acid) gradient. The gradient ran from 30% to 75% acetonitrile-water (containing 0.1% trifluoroacetic acid). Fractions which contained the title compound eluted at 50–58% acetonitrile-water. The fractions were pooled and lyophilized to give 0.89 g (69% yield). Fast atom bombardment mass spectrometry gave observed molecular weight of 602.3 a.m.u.; calculated molecular weight was 602.3 a.m.u.

Example 23

Preparation of N-Boc-D-phenylalanyl-L-prolyl-L-argininal

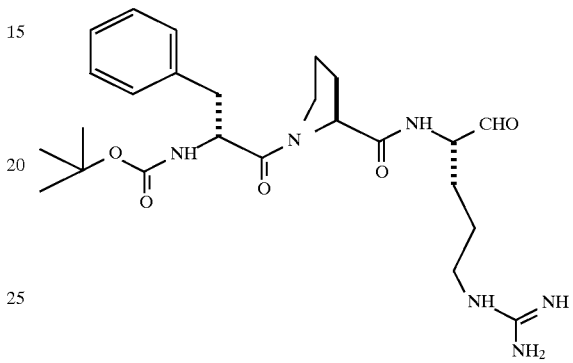

[23]

The above peptide aldehyde [23] has been described as a potent inhibitor of thrombin. See, e.g., Bajusz, S. et al., Folia Haematol. Leipzig, 109: 16 (1982); Bajusz, S., Symposia Biologica Hungarica, 25: 277 (1984); and Bajusz, S. et al., J. Med. Chem., 33: 1729 (1990). Accordingly, it was synthesized for use as a comparison compound in the assays described in Example A.

Peptide aldehyde [23] was synthesized and purified in the same manner as described in Example 8. N-Boc-L-proline was first attached to resin 7 followed by N-Boc-D-phenylalanine. The treatment with 50% trifluoroacetic acid was omitted after the last coupling. The title compound was obtained after further deprotection and purification. Fast atom bombardment mass spectrometry gave observed molecular weight of 502 a.m.u.; calculated molecular weight was 502 a.m.u.

Example 24

Preparation of N-Boc-L-(α-biphenyl)glycine

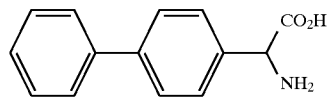

15 g (82 mmole) of 4-biphenylcarboxaldehyde, 3.4 g (63 mmole) of ammonium chloride, 16.4 g (205 mmole) ammonium carbonate and 6.15 g (94 mmoles) of potassium cyanide were dissolved together in 50% ethanol (in deionized water), placed under an atmosphere of argon, then heated for about 12 to 16 hours at 40° C. After this time, the solid which had formed in the mixture was filtered off and washed successively with 25 mL of 50% ethanol (in deionized water), deionized water and diethyl ether to yield 30 g of the hydantoin solid. This solid was dissolved in hot methanol and triturated with deionized water.

4 g of the solid was added to 80 mL of 1M sodium hydroxide and was refluxed for 12 to 16 hours. After this time, 80 mL of ethanol and 3.2 g (80 mmole) of solid sodium hydroxide was added, and the mixture was further refluxed for 12 to 16 hours. The mixture was adjusted to pH 5 with concentrated HCl to yield a solid. The solid was filtered off and dried for 12 to 16 hours under vacuum to yield 2.7 g (75% yield) of the title compound.

Example 25

Preparation of N-t-butoxycarbonyl-D,L-(α-biphenyl)glycyl-L-3-(1-naphthyl)alanyl-L-argininal

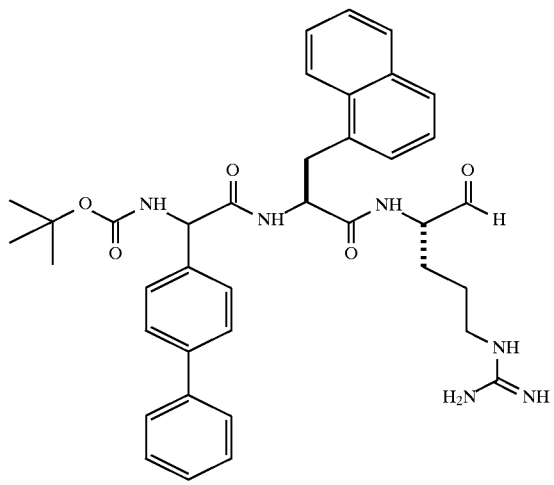

[7]

The above peptide aldehyde was synthesized using an Applied Biosystems Model 430A peptide synthesizer. The Boc chemistry conditions utilized were as provided in the instrument user's manual.

15 Resin 7 (0.67 to 1.00 g, 0.500 mmole amino groups) was made ready for use by removing the Boc protecting groups by treatment with 50% trifluoroacetic acid (in dichloromethane). After washing and neutralizing the acidity by treatment with 10% diisopropylethylamine (in dichloromethane), commercially available Boc-protected amino acids were coupled to the support reagent (and the growing amino acid support chain) in a sequential manner.

Thus, N-Boc-L-3-(1-naphthyl)alanine (2.0 mmole in 2 mL of N-methylmorpholine) was attached to the resin by coupling for one hour with dicyclohexylcarbodiimide (2.0 mmole in 2 mL of N-methylmorpholine) and 1-hydroxybenztriazole (2.0 mmole in 3.3 mL of N-methylmorpholine), followed by treatment with 50% trifluoroacetic acid (in dichloromethane) to remove the Boc protecting group, a wash step and a wash with 10% diisopropylethylamine (in dichloromethane) to neutralize acidity. N-Boc-D,L-α-biphenylglycine was coupled in the same manner. The treatement with 50% trifluoroacetic acid was omitted after the last coupling.

The protected peptide aldehyde was removed from the solid phase, by treatment with a mixture of 5 mL of tetrahydrofuran, 1 mL of acetic acid, 1 mL of formaldehyde and 0.100 mL of 1N hydrochloric acid for 1 hour with stirring. After filtering this mixture, the resin was washed with 10 mL of tetrahydrofuran. The combined filtrates were diluted with 100 mL water and extracted with ethyl acetate. The ethyl acetate phase was then washed with saturated sodium chloride, dried over magnesium sulfate, and concentrated under vacuum.

To remove the nitro and benzyl (where applicable) protecting groups of the peptide aldehyde, the concentrated peptide aldehyde was taken up in a mixture 4.2 mL of methanol, 0.49 mL of 1N hydrochloric acid and 0.250 g of palladium on carbon, then treated with hydrogen at 5 psi for 45 minutes. The mixture was filtered through a fine fritted filter with diatomaceous earth, washed with 10% water in methanol and concentrated to give the crude peptide aldehyde.

The resulting peptide aldehyde was then purified using reverse phase HPLC on a 10 micron particle size, 300 angstrom pore size C-18 column (Vydac), eluting with a water-acetonitrile (both containing 0.1% trifluoroacetic acid) gradient, where the gradient ran from 20% to 50% acetonitrile. The column fractions were analyzed by analytical HPLC and fractions containing pure product were pooled and lyophilized to yield the above-identified product. Fast atom bombardment mass spectrometry gave observed molecular weight of 664.3 a.m.u.; calculated molecular weight was 664.3 a.m.u.

Example 26

Preparation of Mono-O-benzylsuccinic acid

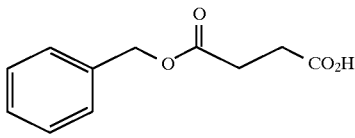

10 g (100 mmole) of succinic anhydride, 10 mL (97 mmole) of benzyl alcohol and 10 mL of triethylamine were combined, the mixture was heated to reflux, allowed to reflux for about 5 minutes, and then was allowed to stir unheated for 1 hour. After this time, the mixture was poured into 250 mL of 1M hydrochloric acid and was extracted with 2–75 mL portions of ethyl acetate. The organic phases were combined, washed with deionized water, washed with brine, and then were dried over anhydrous magnesium sulfate. The organic phase was concentrated to oil which upon sitting yielded crystalline 19.6 g (94% yield) of the title compound.

Example 27

Preparation of N-succinyl-D-phenylalanyl-L-3-(1-naphthyl)alanyl-L-argininal

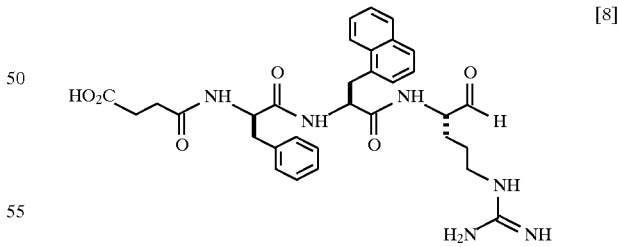

[8]

The above peptide aldehyde was synthesized on the resin in the same manner as described in Example 25. Here, N-Boc-L-3-(1-naphthyl)alanine was first attached to resin 7, followed by N-Boc-D-phenylalanine, followed by mono-O-benzylsuccinic acid.

The titled product as a protected semicarbazone was removed from the solid phase with the concurrent removal of the nitro protecting group, by treating the resin with a mixture of 0.8 mL of anisole and 12.0 mL of hydrofluoric acid at –20° C. for 20 minutes. After removal of the hydrofluoric acid by evaporation at room temperature, the remaining solid was extracted with 50 mL of 0.1M ammonium bicarbonate, followed by 100 mL of deionized water. The extracts were combined and extracted twice with diethyl ether. The aqueous layer was then frozen and lyophilized.

The semicarbazone protecting group was removed by taking up the lyophilized solid in a solution of 5 mL of tetrahydrofuran, 1 mL acetic acid, 0.1 mL of 1M hydrochloric acid and 1 mL of 37% formaldehyde (by weight in water), then allowing the mixture to stir for 1 hour at room temperature. After this time, 20 mL of water was added and the solution was extracted with ethyl acetate. The ethyl acetate phase was then wahsed with saturated sodium chloride, dried over magnesium chloride, and concentrated to about 20 mL under vacuum. 8.6 mL of acetonitrile was added to the cloudy concentrate to yield a clarified solution. The resulting peptide aldehyde is then purified using reverse phase HPLC on a 10 micron particle size, 300 angstrom pore size C-18 column (Vydac), eluting with a water-acetonitrile (both containing 0.1% trifluoroacetic acid) gradient, where the gradient ran from 20% to 50% acetonitrile. The column fractions were analyzed by analytical HPLC and fractions containing pure product were pooled and lyophilized to yield the above-identified product. Fast atom bombardment mass spectrometry gave observed molecular weight of 602.3 a.m.u.; calculated molecular weight was 602.3 a.m.u.

Example 28

Preparation of N-(4-methylpentanyl)-D-phenylalanyl-L-3-(1-naphthyl)alanyl-L-argininal

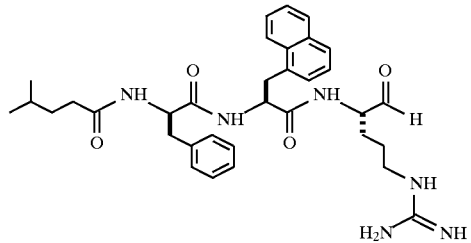

[9]

The above peptide aldehyde was synthesized and purified in the same manner as described in Example 27. Here, N-Boc-L-3-(1-naphthyl)alanine was first attached to resin 7, followed by N-Boc-D-phenylalanine, followed by 4-methylvaleric acid. Fast atom bombardment mass spectrometry gave observed molecular weight of 600.4 a.m.u.; calculated molecular weight was 600.3 a.m.u.

Example 29

N-t-butoxycarbonyl-D-phenylalanyl-L-(3-trans-phenyl)prolinyl-L-argininal

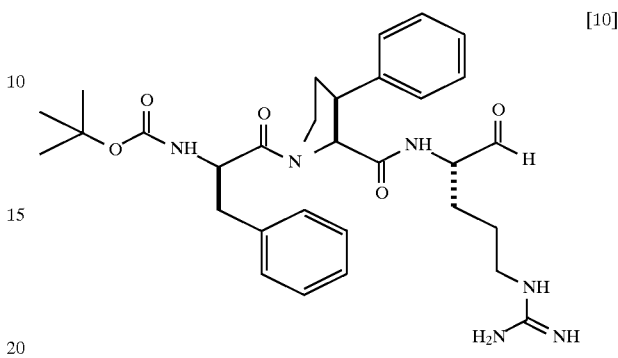

[10]

The above peptide aldehyde was synthesized and purified in the same manner as described in Example 25. Here, N-Boc-L-(3-trans-phenyl)proline was first attached to resin 7, followed by N-Boc-D-phenylalanine.

Example A

Specificity—Determination of $IC_{50}$

The specificity of the peptide aldehydes [1] through [10] was determined in vitro by measurement of their $IC_{50}$ against factor Xa, factor XIa, thrombin and tissue plasminogen activator (tPA). Peptide aldehyde [23] which has been described in the art was run as a comparison. A specific concentration of enzyme and its substrate were challenged with varying concentrations of inhibitor. $IC_{50}$ is that concentration of inhibitor giving 50% inhibition of catalytic activity, under the assay conditions. Specific assay procedures used are presented below.

Table 1 shows the results of these assays for substrate specificity, wherein ">25" means less than 50% inhibition was observed at an inhibitor concentration of 25 $\mu$M. In this table, "β-NpAla" refers to 3-(2-naphthyl)alanine also known as 3-(β-naphthyl)alanine; "PhGly" refers to 2-phenylglycine; and "α-NpAla" refers to 3-(1-naphthyl) alanine also known as 3-(α-naphthyl)alanine.

TABLE 1

Table of $IC_{50}$s for Inhibitors.

| Inhibitor Compound | Compound Number | IC50 ($\mu$M) | | | |
|---|---|---|---|---|---|
| | | Xa | XIa | Thrombin | tPA |
| Boc—D—(β-NpAla)—Phe—Arg—al | [1] | 0.22 | 16 | 14 | >25 |
| Boc—D—PhGly—Phe—Arg—al | [2] | 0.64 | 13 | >25 | >25 |

TABLE 1-continued

Table of IC$_{50}$s for Inhibitors.

| Inhibitor Compound | Compound Number | IC50 ($\mu$M) | | | |
|---|---|---|---|---|---|
| | | Xa | XIa | Thrombin | tPA |
| Boc—D—Phe—β-NpAla—Arg—al | [3] | 0.89 | 25 | 25 | >25 |
| Boc—D—Phe—Phe—Arg—al | [4] | 0.21 | 25 | >25 | >25 |
| Boc—D—Phe—(α-NpAla)—Arg—al | [5] | 0.030 | 14 | 13 | >25 |
| Ac—D—Phe—(α-NpAla)—Arg—al | [6] | 0.025 | 0.32 | >25 | >25 |
| Boc—L—BPGly-(α-NpAla)—Arg—al | [7] | 2.5 | >25 | >25 | >25 |
| Succ—D—Phe—(α-NpAla)—Arg—al | [8] | 0.023 | 20 | >25 | >25 |
| 4MeV—D—Phe—(α-NpAla)—Arg—al | [9] | 0.17 | >25 | >25 | — |
| Boc—D—Phe—(3-trans-PhPro)—Arg—al | [10] | 0.625 | >25 | >25 | >25 |
| Boc—D—Phe—Pro—Arg—al | [23] | 5.7 | 1.8 | 0.025 | 1.1 |

Table 2 shows the Percent Selectivity for exemplar compounds of the present invention. Percent Selectivity is defined as the 100 times the IC$_{50}$ for factor Xa divided by the IC$_{50}$ of either factor XIa, thrombin or tPA. The Percent Selectivity of each inhibitor for factor Xa is taken as 100. Accordingly, a Percent Selectivity of less than 100 for a given inhibitor factor XIa, thrombin or tPA is indicative of weakly inhibiting activity, if active at all to inhibit those enzymes while strongly inhibiting factor Xa.

TABLE 2

Table of Percent Selectivity for Inhibitors.

| Inhibitor Compound | Compound Number | Percent Selectivity | | | |
|---|---|---|---|---|---|
| | | Xa | XIa | Thrombin | tPA |
| Boc—D—(β-NpAla)—Phe—Arg—al | [1] | 100 | 1.4 | 1.6 | <0.9 |
| Boc—D—PhGly—Phe—Arg—al | [2] | 100 | 4.9 | <2.6 | <2.6 |
| Boc—D—Phe—(β-NpAla)—Arg—al | [3] | 100 | 3.6 | 3.6 | <3.6 |
| Boc—D—Phe—Phe—Arg—al | [4] | 100 | 0.8 | <0.8 | <0.8 |
| Boc—D—Phe—(α-NpAla)—Arg—al | [5] | 100 | 0.2 | 0.2 | <0.1 |
| Ac—D—Phe—(α-NpAla)—Arg—al | [6] | 100 | 7.8 | <0.1 | <0.1 |
| Boc—D,L—BPGly-(α-NpAla)—Arg—al | [7] | 100 | <10 | <10 | <10 |
| Succ—D—Phe—(α-NpAla)—Arg—al | [8] | 100 | 0.12 | <0.1 | <0.1 |
| MeV—D—Phe—(α-NpAla)—Arg—al | [9] | 100 | <0.68 | <0.68 | — |
| Boc—D—Phe—(3-trans-PhPro)—Arg—al | [10] | 100 | <2.5 | <2.5 | <2.5 |
| Boc—D—Phe—Pro—Arg—al | [23] | 100 | 317 | 22,800 | 518 |

(a) Factor Xa Assay.

Enzyme activity was determined using as substrate, S2765 (N-α-benzyloxycarbonyl-D-argininyl-L-glycyl-L-arginine-p-nitroanilide dihydrochloride) which was obtained from Kabi Diagnostica. The substrate was made up in deionized water prior to use.

Human factor Xa was obtained from Enzyme Research Laboratories. The enzyme was diluted into TBSA prior to use.

The assay was run by combining in appropriate wells 50 $\mu$L of TBSA, 50 $\mu$L of inhibitor in TBSA or TBSA (as negative control) and 50 $\mu$L of 2 nM human Factor Xa or TBSA (as background control). After incubating this mixture for 60 minutes at room temperature, 50 $\mu$L of 1 mM S-2765 was added to each well and the initial rate of the change of the optical density at 405 nm (OD$_{405nm}$) for each well was determined. OD$_{405nm}$ was measured every 10 seconds for 5 minutes.

(b) Factor XIa Assay.

Enzyme activity was determined using as substrate, S2366 (L-pyroglutamyl-L-prolyl-L-arginine-p-nitroanilide hydrochloride) which was obtained from Kabi Diagnostica. The substrate was made up in deionized water prior to use.

Human factor XIa was obtained from Enzyme Research Laboratories, Inc. The enzyme was diluted into TBSA prior to use.

The assay was run by combining in appropriate wells 50 $\mu$L of TBSA, 50 $\mu$L of inhibitor in TBSA or TBSA (as negative control) and 50 $\mu$L of 2 nM human Factor XIa or TBSA (as background control). After incubating this mixture for 60 minutes at room temperature, 50 $\mu$L of 6 mM S-2366 was added to each well and the initial rate of the change of the optical density at 405 nm (OD$_{405nm}$) for each well was determined. OD$_{405nm}$ was measured every 10 seconds for 5 minutes.

(c) Thrombin Assay.

Enzyme activity was determined using as substrate, S2238 (D-phenylalanyl-L-pipecolyl-L-arginine-p-nitroanilide dihydrochloride) which was obtained from Kabi Diagnostica. The substrate was made up in deionized water prior to use.

Human α-thrombin was obtained from Enzyme Research Laboratories, Inc. The enzyme was diluted into TBSA prior to use.

The assay was run by combining in appropriate wells 50 $\mu$L of TBSA, 50 $\mu$L of inhibitor in TBSA or TBSA (as negative control) and 50 $\mu$L of 4 nM human α-thrombin or TBSA (as background control). After incubating this mixture for 60 minutes at room temperature, 50 $\mu$L of 0.24 mM S-2238 was added to each well and the initial rate of the change of optical density at 405 nm (OD$_{405nm}$) for each well was determined. OD$_{405nm}$ was measured every 10 seconds for 5 minutes.

(d) tPA Assay.

Enzyme activity was determined using as substrate, Pefachrome tPA (O-methylsulfonate-D-hexahydrotyrosine-L-glycyl-L-argini ne-p-nit roanilide acetate salt) which was obtained from Centerchem, Inc. The substrate was made up in deionized water prior to use.

Human recombinant t-PA (Activase®) was obtained from Genentech, Inc. The enzyme was reconstituted with water, then diluted into TBSA prior to use.

The assay was run by combining in appropriate wells 50 µL of TBSA, 50 µL of inhibitor in TBSA or TBSA (as negative control) and 50 µL of 4 nM human recombinant tPA or TBSA (as background control). After incubating this mixture for 60 minutes at room temperature, 50 µL of 4 mM Pefachrome tPA was added to each well and the initial rate of the change of optical density at 405 nm ($OD_{405nm}$) for each well was determined. $OD_{405nm}$ was measured every 10 seconds for 5 minutes.

We claim:

1. A compound of the formula:

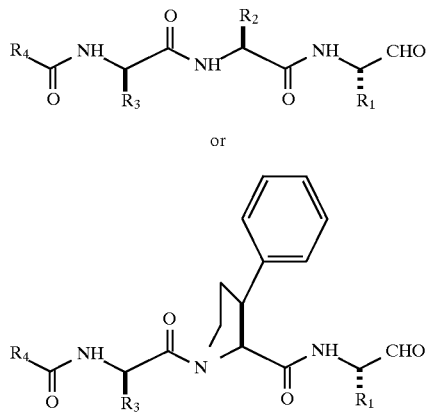

wherein $R_1$ is selected from the group consisting of —$(CH_2)_3$—NH—C(=NH)—$NH_2$ and alkyl- and di-alkyl-substituted derivatives of —$(CH_2)_3$—NH—C(=NH)—$NH_2$, wherein each alkyl group is independently selected and has 1 to about 7 carbon atoms;

$R_2$ is selected from the group consisting of aralkyl of 7 to about 15 carbon atoms optionally substituted with 1 to 2 independently selected alkyl groups of 1 to about 4 carbon atoms;

$R_3$ is selected from the group consisting of aryl of about 6 to about 14 carbon atoms optionally substituted with 1 to 2 independently selected alkyl groups of 1 to about 4 carbon atoms, aralkyl of about 7 to about 15 carbon atoms optionally substituted with 1 to 2 independently selected alkyl groups of 1 to about 4 carbon atoms, and cyclohexylmethyl; and $R_4$ is selected from the group consisting of alkyl of 1 to about 12 carbon atoms, alkenyl of about 3 to about 6 carbon atoms, aryl of about 6 to about 14 carbon atoms, aralkyl of about 7 to about 15 carbon atoms, alkoxy of 1 to about 12 carbon atoms, alkenyloxy of about 3 to about 8 carbon atoms, aryloxy of about 6 to about 14 carbon atoms, aralkyloxy of about 7 to about 15 carbon atoms and carboxyalkyl of 2 to about 7 carbon atoms; or a pharmaceutically acceptable salts thereof.

2. A compound according to claim 1, wherein $R_1$ is —$(CH_2)_3$—NH—C(=NH)—$NH_2$.

3. A compound of claim 2, wherein $R_2$ is selected from the group consisting of phenylmethyl, diphenylmethyl, biphenylmethyl and napthylmethyl, each optionally ring substituted with 1 to 2 independently selected alkyl groups of having 1 to about 4 carbon atoms; and $R_3$ is selected from the group consisting of phenyl, phenylmethyl, diphenylmethyl, biphenyl, biphenylmethyl, napthyl, or napthylmethyl, each optionally ring substituted with 1 to 2 independently selected alkyl groups of 1 to about 4 carbon atoms.

4. A compound of claim 3, wherein $R_2$ is selected from the group consisting of phenylmethyl, 1-naphthylmethyl and 2-naphthylmethyl and $R_3$ is selected from the group consisting of phenyl, phenylmethyl, and 2-napthylmethyl.

5. A compound of claim 4, wherein $R_4$ is selected from the group consisting of methyl, ethyl, 1,1-dimethylethyl, propyl, 2-methylpropyl, 2,2-dimethylpropyl, butyl, pentyl, hexyl, cyclopentyl, cyclopentylmethyl, cyclohexyl, cyclohexylmethyl, adamantyl, adamantylmethyl, 2-propenyl, 3-butenyl, 1-pentenyl, 2-pentenyl, 5-hexenyl, 2-cyclopentenyl, phenyl, phenylmethyl, diphenylmethyl, biphenyl, biphenylmethyl, napthyl, napthylmethyl, 1,1-dimethylethyloxy, 2-methylpropyloxy, 2,2-dimethylpropyloxy, cyclopentyloxy, cyclopentylmethyloxy, cyclohexyloxy, cyclohexylmethyloxy, adamantyloxy, adamantylmethoxy, phenoxy, benzyloxy, biphenylmethyloxy, naphthyloxy, napthylmethyloxy, and 2-carboxyethyl.

6. A compound of claim 5, wherein $R_4$ is 1,1-dimethylethyloxy.

7. A compound of claim 5, wherein $R_4$ is methyl.

8. A compound of claim 5, wherein $R_4$ is 2-carboxyethyl.

9. A compound of claim 2 wherein $R_4$ is selected from the group consisting of alkyl of 1 to about 12 carbon atoms, alkoxy of 1 to about 12 carbon atoms, and carboxyalkyl of 2 to about 7 carbon atoms.

10. A compound of claim 2 selected from the group consisting of:

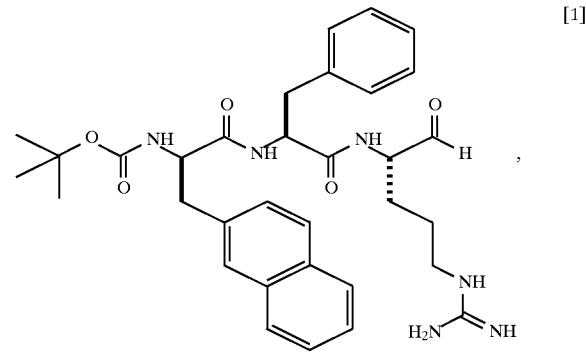

[1]

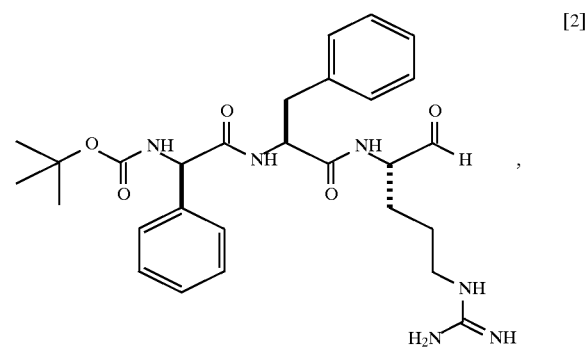

[2]

-continued
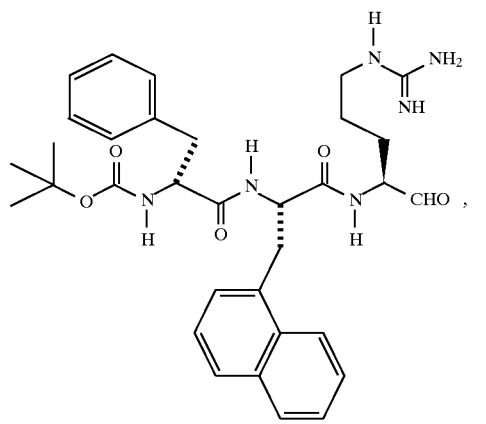  [3]
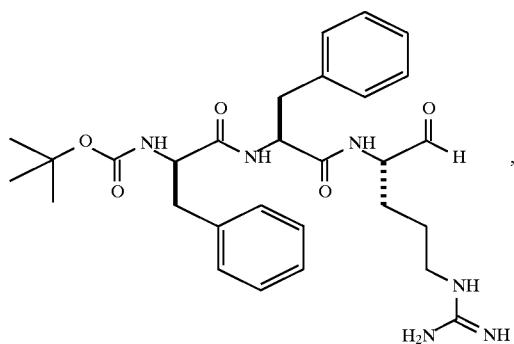  [4]
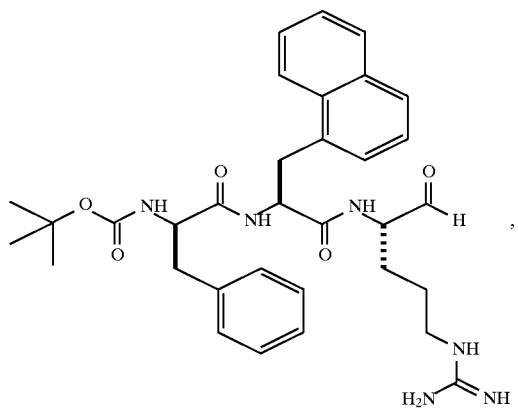  [5]
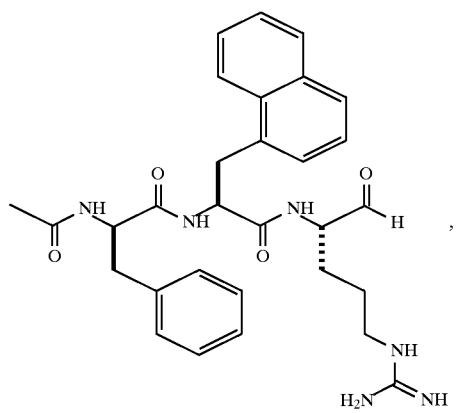  [6]
-continued
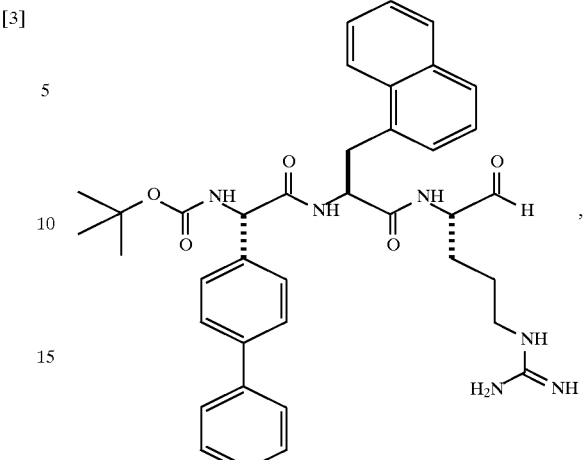  [7]
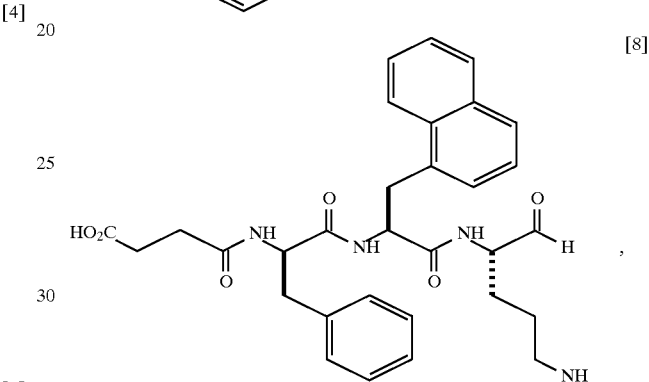  [8]
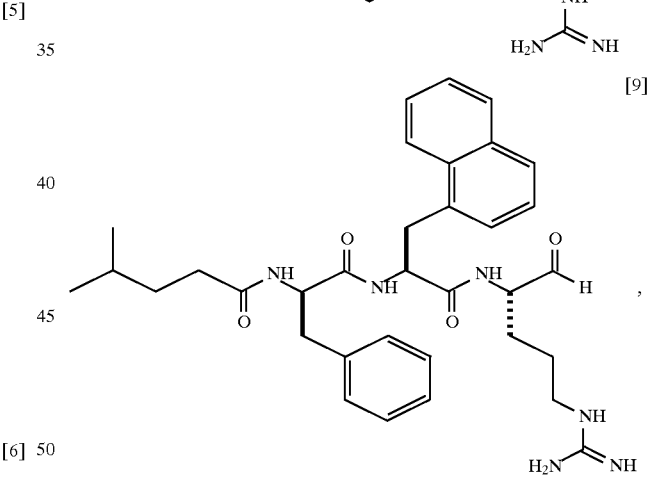  [9]
and
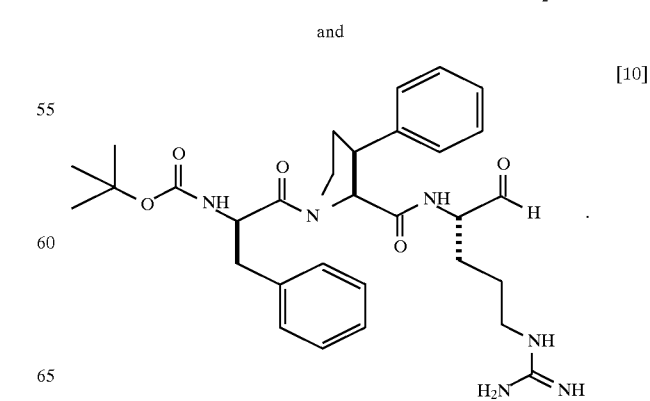  [10]

11. A pharmaceutical composition for treating or decreasing the incidence of a condition characterized by abnormal thrombus formation in a mammal comprising a pharmaceutically acceptable carrier and a therapeutically effective amount of compound of claim 2, 3, 4, 5, 6, 7, 8, 9, or 10 effective to decrease abnormal thrombus formation.

12. A method treating or decreasing the incidence of a condition characterized by abnormal thrombus formation in a mammal comprising administering to said mammal a therapeutically effective amount of the compound of claim 2, 3, 4, 5, 6, 7, 8, 9, or 10 effective to decrease abnormal thrombus formation.

13. A method for treating or decreasing the incidence of a condition characterized by abnormal thrombus formation in a mammal comprising administering to said mammal a therapeutically effective amount of the composition of claim 11 effective to decrease abnormal thrombus formation.

* * * * *